US012584046B2

(12) United States Patent
Ito et al.

(10) Patent No.: US 12,584,046 B2
(45) Date of Patent: Mar. 24, 2026

(54) GAS GENERATING AGENT, PRESSURE-SENSITIVE ADHESIVE COMPOSITION AND PRESSURE-SENSITIVE ADHESIVE SHEET

(71) Applicant: DAI NIPPON PRINTING CO., LTD., Tokyo-to (JP)

(72) Inventors: Yohei Ito, Tokyo-to (JP); Michihiro Ogura, Tokyo-to (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 355 days.

(21) Appl. No.: 18/269,072

(22) PCT Filed: Dec. 22, 2021

(86) PCT No.: PCT/JP2021/047514

§ 371 (c)(1),
(2) Date: Jun. 22, 2023

(87) PCT Pub. No.: WO2022/138703

PCT Pub. Date: Jun. 30, 2022

(65) Prior Publication Data

US 2024/0141213 A1 May 2, 2024

(30) Foreign Application Priority Data

Dec. 25, 2020 (JP) ................................ 2020-217124

(51) Int. Cl.

*C09J 11/06* (2006.01)
*C07D 257/04* (2006.01)
*C09J 7/38* (2018.01)

(52) U.S. Cl.

CPC ............ *C09J 11/06* (2013.01); *C07D 257/04* (2013.01); *C09J 7/385* (2018.01); *C09J 2301/302* (2020.08); *C09J 2301/416* (2020.08); *C09J 2301/502* (2020.08); *C09J 2433/00* (2013.01)

(58) Field of Classification Search

None
See application file for complete search history.

(56) References Cited

U.S. PATENT DOCUMENTS

2010/0279050 A1* 11/2010 Ootake .................. B32B 27/30 428/41.5
2013/0071658 A1* 3/2013 Nomura ................ H01L 21/027 524/106

FOREIGN PATENT DOCUMENTS

JP H05-32946 A 2/1993
JP 2003-231872 A 8/2003
WO 2011/118506 A1 9/2011

* cited by examiner

*Primary Examiner* — Sheeba Ahmed
(74) *Attorney, Agent, or Firm* — Oliff PLC

(57) ABSTRACT

A gas generating agent which generates a gas by light irradiation, which has a maximum molar absorption coefficient value of 7000 or more at a wavelength of 240 nm to 450 nm, and which contains a gas generating moiety having a specific structure and an organopolysiloxane group or a fluorinated aliphatic hydrocarbon group in which a number of carbon atoms to which a fluorine atom is directly bound is from 2 to 8 and which optionally contains an ether bond (—O—) in a carbon chain.

10 Claims, 1 Drawing Sheet

GAS GENERATING AGENT, PRESSURE-SENSITIVE ADHESIVE COMPOSITION AND PRESSURE-SENSITIVE ADHESIVE SHEET

TECHNICAL FIELD

The disclosure relates to a gas generating agent, a pressure-sensitive adhesive composition containing the gas generating agent, and a pressure-sensitive adhesive sheet containing the gas generating agent.

BACKGROUND ART

A pressure-sensitive adhesive composition containing a pressure-sensitive adhesive component is widely used in binder agents such as a pressure-sensitive adhesive, a sealing agent, a paint and a coating agent, and in pressure-sensitive adhesive materials such as a pressure-sensitive adhesive tape and a pressure-sensitive adhesive sheet. Performances required of the pressure-sensitive adhesive composition vary depending on its applications. In some cases, depending on its applications, the pressure-sensitive adhesive composition is needed to show adhesion for a required period of time and allow easy peeling after the period of time.

For example, in a semiconductor chip production process, it is proposed that processes be efficiently performed by, in the process of producing a thin wafer by cutting a thick wafer from high-purity silicon single-crystal or the like and polishing the thick wafer to a given thickness, attaching the thick wafer to a pressure-sensitive adhesive sheet for reinforcement. Even in the case of grinding a thin wafer to a given thickness and dicing the wafer into semiconductor chips, a pressure-sensitive adhesive sheet called “dicing tape” is used as a support for temporary fixation. Also, a pressure-sensitive adhesive sheet is used as a support for temporary fixation when cutting a sheet, which is obtained by pressure-bonding stacked dielectric paste sheets on which an electrode is printed, into chips in a multi-layer ceramic capacitor (MLCC) production process. Also, a pressure-sensitive adhesive sheet is used as a support for temporary fixation for processes in a flexible printed circuit production process. In a flexible printed circuit production process or a flexible organic EL display production process, a protection sheet for protecting the surface of a substrate used in the above printed circuit or display is sometimes used for the purpose of preventing the substrate from scratches or contamination by chemicals, from degradation of the substrate by heat or chemicals used in the production process, and so on. In this case, a pressure-sensitive adhesive sheet is used as the temporary protection sheet.

The process pressure-sensitive adhesive material used in the production process is needed to adhere firmly during the process and to allow the removal of the obtained thin wafer, semiconductor chips or the like without damage after the process (hereinafter, it may be referred to as “high adhesion and easy peel”).

As a pressure-sensitive adhesive material directed to high adhesion and easy peel, Patent Document 1 discloses a pressure-sensitive adhesive tape using a photocurable pressure-sensitive adhesive that is curable by light irradiation (e.g., UV irradiation) and shows a decrease in pressure-sensitive adhesion once cured. Patent Document 1 mentions that while the pressure-sensitive adhesive tape attaches during processing, it can easily peel off by UV irradiation or the like. However, this pressure-sensitive adhesive tape shows an insufficient decrease in pressure-sensitive adhesion after UV irradiation or the like, and it is difficult to peel off a thin wafer, semiconductor chips or the like without damage.

Patent Document 2 discloses a pressure-sensitive adhesive tape having a pressure-sensitive adhesive layer that contains a gas generating agent such as an azo compound, which generates a gas by stimulation. It is described that when stimulation is applied to the pressure-sensitive adhesive tape, the gas generated from the gas generating agent is released to the interface between the tape and the adherend; the released gas separates at least a part of the adherend; and accordingly, a thin wafer, semiconductor chips or the like can be peeled off without damage and without adhesive residue.

As an adhesive composition having high adhesion as well as being easily detachable and having excellent heat resistance, Patent Document 3 proposes a pressure-sensitive adhesive composition using a tetrazole compound which generates a gas by light irradiation and which has high heat resistance.

However, there is the following problem: even when the above-described azo compound or tetrazole compound is used, a decrease in peel adhesion is insufficient, or the amount of the added compound needs to be increased for a sufficient decrease in peel adhesion.

CITATION LIST

Patent Documents

Patent Document 1: Japanese Patent Application Laid-Open (JP-A) No. H5-32946

Patent Document 2: JP-A No. 2003-231872

Patent Document 3: International Publication No. WO2011/118506

SUMMARY OF INVENTION

Technical Problem

For elaboration and complication of various kinds of electronic components and the like, decreasing the thickness of an adherend, integrating the functions of an adherend, and miniaturizing an adherend have been developed. Along with them, the adherend or its surface is easily damaged. Accordingly, there is a demand for such easy peeling, that while firm adhesion is achieved during the processes, less load is applied on the adherend after the processes.

However, there is a trade-off relationship between increasing pressure-sensitive adhesion and improving easy peel properties, and conventional pressure-sensitive adhesive materials directed to high adhesion and easy peel are still insufficient in easy peel properties.

The present disclosure was achieved in light of the above circumstances. An object of the present disclosure is to provide the following: a gas generating agent which generates a gas by light irradiation and which can increase the effect of imparting peel properties to the surface; a pressure-sensitive adhesive composition using the gas generating agent, which can form a pressure-sensitive adhesive layer that shows, while having sufficient pressure-sensitive adhesion in use, excellent easy peel properties from an adherend when peeled off; and a pressure-sensitive adhesive sheet using the pressure-sensitive adhesive composition, which shows excellent easy peel properties from an adherend while having sufficient pressure-sensitive adhesion in use.

Solution to Problem

In a first embodiment of the present disclosure, there is provided a gas generating agent which generates a gas by light irradiation, which has a maximum molar absorption coefficient value of 7000 or more at a wavelength of 240 nm to 450 nm, and which is represented by at least one of the following general formulae (1) and (2):

$$A\text{-}L\text{-}Q^1 \quad (1)$$

$$A\text{-}L\text{-}Q^2\text{-}L\text{-}A \quad (2)$$

in the general formulae (1) and (2), each A is independently a gas generating moiety represented by the following general formula (A-1), (A-2) or (A-3); each L is independently a direct bond or a divalent linking group; $Q^1$ is a monovalent fluorinated aliphatic hydrocarbon group in which a number of carbon atoms to which a fluorine atom is directly bound is from 2 to 8, which optionally contains an ether bond (—O—) in a carbon chain, and which optionally contains a substituent, or $Q^1$ is a monovalent organopolysiloxane group; and $Q^2$ is a divalent fluorinated aliphatic hydrocarbon group in which a number of carbon atoms to which a fluorine atom is directly bound is from 2 to 8 and which optionally contains an ether bond (—O—) in a carbon chain, or $Q^2$ is a divalent organopolysiloxane group:

(A-1)

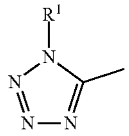

(A-2)

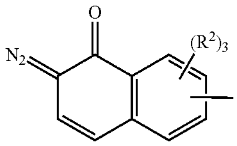

(A-3)

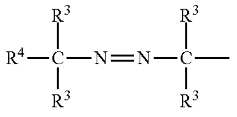

in the general formulae (A-1), (A-2) and (A-3), $R^1$ is an aromatic group which contains 3 to 20 carbon atoms and which optionally contains a substituent; each $R^2$ is independently a hydrogen atom or a hydrocarbon group which contains 1 to 20 carbon atoms and which optionally contains a substituent; each $R^3$ is independently a hydrocarbon group which contains 1 to 20 carbon atoms and which optionally contains a substituent, a cyano group, $—COOR^5$ or $—CONR^6 R^7$; $R^4$ is a hydrocarbon group which contains 1 to 20 carbon atoms and which optionally contains a substituent, a cyano group, $—COOR^5$, $—CONR^6R^7$ or the above-described $-L-Q^1$; each $R^3$ is independently a hydrocarbon group which contains 1 to 20 carbon atoms and which optionally contains a substituent; each $R^7$ is independently a hydrocarbon group which contains 1 to 20 carbon atoms and which optionally contains a substituent; and $R^6$ is a hydrogen atom or a hydrocarbon group which contains 1 to 5 carbon atoms.

In the general formulae (1) and (2) of the gas generating agent of the present disclosure, $Q^1$ may be any one of monovalent fluorinated aliphatic hydrocarbon groups represented by the following formulae (Rf-1) to (Rf-5) or a monovalent organopolysiloxane group represented by the following formula (Si-1), and $Q^2$ may be a divalent fluorinated aliphatic hydrocarbon group represented by the following formula (Rf-6) or a divalent organopolysiloxane group represented by the following formula (Si-2):

$$—C_nF_{2n+1} \quad \text{(Rf-1)}$$

$$—C_nF_{2n}H \quad \text{(Rf-2)}$$

$$—C_nF_{2n-1} \quad \text{(Rf-3)}$$

$$—C_{n'}F_{2n'-3} \quad \text{(Rf-4)}$$

$$—C_nF_{2n}—(OC_{n''}F_{2n''})_m—J^1 \quad \text{(Rf-5)}$$

$$—C_nF_{2n}—(OC_{n''}F_{2n''})_m— \quad \text{(Rf-6)}$$

in the formulae (Rf-1), (Rf-2) and (Rf-3), each n is independently an integer of 2 to 8;

in the formula (Rf-4), n' is an integer of 4 to 10;

in the formula (Rf-5), n is an integer of 1 to 8; n" is an integer of 0 to 7; m is an integer of 0 to 7; n+n"×m is an integer of 2 to 8; and $J^1$ is a hydrogen atom, a fluorine atom, a hydroxyl group, an amino group, a carboxy group or a (meth)acryloyloxy group;

in the formula (Rf-6), n is an integer of 0 to 8; n" is an integer of 0 to 4; m is an integer of 0 to 8; and n+n"×m is an integer of 2 to 8;

(Si-1)

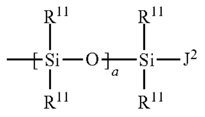

(Si-2)

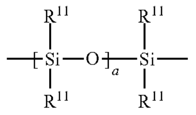

In the formulae (Si-1) and (Si-2), each $R^{11}$ is independently a monovalent hydrocarbon group which contains 1 to 20 carbon atoms and which optionally contains a substituent, a hydrogen atom, a hydroxyl group, an alkoxy group which contains 1 to 20 carbon atoms, or a group represented by the following formula (Si-3); $J^2$ is a monovalent hydrocarbon group which contains 1 to 20 carbon atoms and which optionally contains a substituent, a hydrogen atom, a hydroxyl group, an alkoxy group which contains 1 to 20 carbon atoms, an amino group, a carboxy group or a (meth)acryloyloxy group; and each a is independently a number of 1 to 100; and (Si-3)

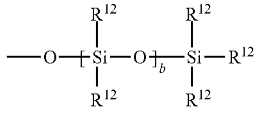

in the formula (Si-3), each $R^{12}$ is independently a monovalent hydrocarbon group which contains 1 to 20 carbon atoms and which optionally contains a substituent, a hydrogen atom, a hydroxyl group or an alkoxy group which contains 1 to 20 carbon atoms, and b is a number of 0 to 100.

In the general formulae (1) and (2) of the gas generating agent of the present disclosure, each L may be independently a direct bond, $—SCH_2CH_2COO—$, $—SCH_2CH(CH_3)COO—$, $—SCH_2CH(OH)CH_2—$, $—OCH_2CH(OH)CH_2—$, $—SCH(CH_3)O—$, $—OCH(CH_3)O—$, —COO—, —CONH—, —COS—, $—SO_2NH—$, or a hydrocarbon group which contains 1 to 22 carbon atoms, which optionally contains at least one selected from the group consisting of —O— and —S—, and which is optionally substituted by a hydroxyl group, or a combination thereof.

In another embodiment of the present disclosure, there is provided a pressure-sensitive adhesive composition comprising a pressure-sensitive adhesive component and the gas generating agent of the first embodiment of the present disclosure.

In another embodiment of the present disclosure, there is provided a pressure-sensitive adhesive sheet comprising a pressure-sensitive adhesive layer and a substrate or release sheet on one surface of the pressure-sensitive adhesive layer, wherein the pressure-sensitive adhesive layer is a pressure-sensitive adhesive composition comprising a pressure-sensitive adhesive component and the gas generating agent of the first embodiment of the present disclosure, or a cured product of the pressure-sensitive adhesive composition, and wherein the pressure-sensitive adhesive layer has a property that a decrease in pressure-sensitive adhesion from an initial pressure-sensitive adhesion is caused by light irradiation.

The pressure-sensitive adhesive composition of the present disclosure or the pressure-sensitive adhesive composition in the pressure-sensitive adhesive sheet of the present disclosure may further comprise a photocurable component and a photoinitiator.

The pressure-sensitive adhesive composition of the present disclosure or the pressure-sensitive adhesive composition in the pressure-sensitive adhesive sheet of the present disclosure may further comprise a thermal crosslinking agent.

The pressure-sensitive adhesive sheet of the present disclosure may further comprise a release sheet on a surface on an opposite side of the pressure-sensitive adhesive layer to the substrate or release sheet side.

Advantageous Effects of Invention

According to the embodiments of the present disclosure, the following are provided: a gas generating agent which generates a gas by light irradiation and which can increase the effect of imparting peel properties to the surface; a pressure-sensitive adhesive composition using the gas generating agent, which can form a pressure-sensitive adhesive layer that shows, while having sufficient pressure-sensitive adhesion in use, excellent easy peel properties from an adherend when peeled off; and a pressure-sensitive adhesive sheet using the pressure-sensitive adhesive composition, which shows excellent easy peel properties from an adherend while having sufficient pressure-sensitive adhesion in use.

BRIEF DESCRIPTION OF DRAWINGS

In the accompanying drawings.

DESCRIPTION OF EMBODIMENTS

Figure 1:
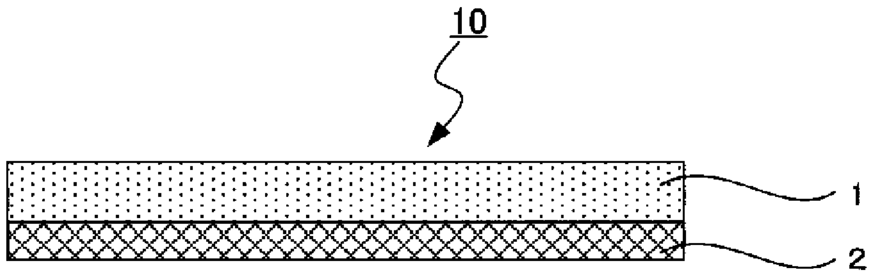
FIG. 1 is a schematic sectional view of an example of the pressure-sensitive adhesive sheet of the present disclosure.

Hereinafter, descriptions will be made about embodiments, working examples and others in the present disclosure with reference to the drawings and so on. However, about the present disclosure, many different embodiments can be carried out. Thus, the present invention should not be interpreted with any limitation to described contents of the embodiments, the working examples, and the others, which will be given as examples. In order to make a description about each of the drawings clearer, the width, the thickness, the shape and any other factors of each part or portion therein may be schematically illustrated, differently from that of a part or portion in an actual form. However, the illustrated factors are each a mere example not to limit the interpretation of the present disclosure. In the document DESCRIPTION, and each of the drawings, to the same element as in any one of the drawings referred to already is attached the same reference number; thus, a detailed description thereabout is appropriately omitted. For the convenience of the descriptions, any word such as a word "upward" or "downward" may be used. However, the upward and downward directions may also be reversed.

In the DESCRIPTION, in a case where, for example, any member or a constituent of any region is "on (or beneath) of a different member or a constituent of a different region, examples of this case include not only a case where the member is just on (or just beneath) of the different constituent, but also a case where the member or the constituent is over or above (or under or below) of the different constituent, that is, a case where an additional member is included between the two to be over or above (or under or below) the constituent unless otherwise specified.

In the present disclosure, (meth)acryl means each of acryl and methacryl, and (meth)acrylate means each of acrylate and methacrylate.

In the DESCRIPTION, the term "sheet" includes a component called "film". The term "film" includes a component called "sheet". The term "sheet surface (film surface)" refers to a surface corresponding to, when a target sheet-shaped (film-shaped) component is viewed wholly from a large perspective, the planar direction of the target sheet-shaped component (film-shaped component).

In the present disclosure, the term "light" encompasses lights including ultraviolet light.

Hereinafter, detailed descriptions are given for the gas generating agent, pressure-sensitive adhesive composition and pressure-sensitive adhesive sheet of the present disclosure.

A. Gas Generating Agent

In one embodiment of the present disclosure, there is provided a gas generating agent which generates a gas by light irradiation, which has a maximum molar absorption coefficient value of 7000 or more at a wavelength of 240 nm to 450 nm, and which is represented by at least one of the following general formulae (1) and (2):

$$A\text{-}L\text{-}Q^1 \qquad (1)$$

$$A\text{-}L\text{-}Q^2\text{-}L\text{-}A \qquad (2)$$

in the general formulae (1) and (2), each A is independently a gas generating moiety represented by the following general formula (A-1), (A-2) or (A-3); each L is independently a direct bond or a divalent linking group; $Q^1$ is a monovalent fluorinated aliphatic hydrocarbon group in which a number of carbon atoms to which a fluorine atom is directly bound is from 2 to 8, which optionally contains an ether bond (—O—) in a carbon chain, and which optionally contains a substituent, or $Q^1$ is a monovalent organopolysiloxane group; and $Q^2$ is a divalent fluorinated aliphatic hydrocarbon group in which a number of carbon atoms to which a fluorine atom is directly bound is from 2 to 8 and which optionally contains an ether bond (—O—) in a carbon chain, or $Q^2$ is a divalent organopolysiloxane group:

(A-1)

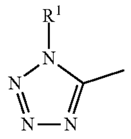

(A-2)

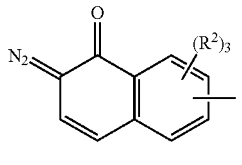

(A-3)

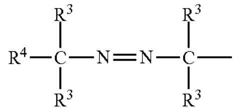

in the general formulae (A-1), (A-2) and (A-3), $R^1$ is an aromatic group which contains 3 to 20 carbon atoms and which optionally contains a substituent; each $R^2$ is independently a hydrogen atom or a hydrocarbon group which contains 1 to 20 carbon atoms and which optionally contains a substituent; each $R^3$ is independently a hydrocarbon group which contains 1 to 20 carbon atoms and which optionally contains a substituent, a cyano group, $—COOR^5$ or $—CONR^6 R^7$; $R^4$ is a hydrocarbon group which contains 1 to 20 carbon atoms and which optionally contains a substituent, a cyano group, $—COOR^5$, $—CONR^6R^7$ or the above-described $-L-Q^1$; each $R^5$ is independently a hydrocarbon group which contains 1 to 20 carbon atoms and which optionally contains a substituent; each $R^7$ is independently a hydrocarbon group which contains 1 to 20 carbon atoms and which optionally contains a substituent; and $R^6$ is a hydrogen atom or a hydrocarbon group which contains 1 to 5 carbon atoms.

The gas generating agent of the present disclosure contains the gas generating moiety having the above-specified structure and the above-specified fluorinated aliphatic hydrocarbon group or organopolysiloxane group, and it is a gas generating agent which generates a gas by light irradiation and which has the maximum molar absorption coefficient value of 7000 or more at a wavelength of 240 nm to 450 nm. Accordingly, the gas generating agent of the present disclosure is a gas generating agent that can increase the effect of imparting peel properties to the surface. The reason for this is not clear; however, it is presumed as follows.

In the pressure-sensitive adhesive layer containing the gas generating agent directed to high adhesion and easy peel, by light irradiation after use, the gas generated from the gas generating agent is released to the surface of the pressure-sensitive adhesive layer, that is, the interface with the adherend, and at least a part of the adherend peels off by the resulting pressure. By the release of the gas to the pressure-sensitive adhesive layer surface, the contact area between the pressure-sensitive adhesive layer and the adherend is decreased, and the pressure-sensitive adhesive layer can easily peel off. In a pressure-sensitive adhesive layer containing a conventional gas generating agent, the gas generating agent is uniformly disperse in the pressure-sensitive adhesive layer. Accordingly, even when irradiated with light, a gas is less likely to be released to the surface of the pressure-sensitive adhesive layer from the gas generating agent present inside the pressure-sensitive adhesive layer, and the amount of only the gas generated from the gas generating agent present near the pressure-sensitive adhesive layer surface, is not enough of the gas amount needed to be generated on the pressure-sensitive adhesive layer surface. Accordingly, a decrease in the peel adhesion is insufficient, and the easy peel properties are insufficient. When the content of the gas generating agent in the pressure-sensitive adhesive layer is increased to increase the generated gas amount on the pressure-sensitive adhesive layer surface, a decrease in the pressure-sensitive adhesion of the pressure-sensitive adhesive layer and clouding of the pressure-sensitive adhesive layer occur. Accordingly, there is a limit to increasing the peel adhesion by the addition of the gas generating agent.

In the gas generating agent of the present disclosure, the above-specified fluorinated aliphatic hydrocarbon group or organopolysiloxane group is introduced into the gas generating moiety having the above-specified structure. Accordingly, the gas generating agent is likely to localize on the surface. In the pressure-sensitive adhesive layer containing the gas generating agent of the present disclosure, since the gas generating agent is likely to localize on the surface of the pressure-sensitive adhesive layer, when irradiated with light, the gas generating agent localized on the pressure-sensitive adhesive layer surface generates a gas, and the gas is likely to be released to the surface of the pressure-sensitive adhesive layer. Since the generated gas amount on the pressure-sensitive adhesive layer surface efficiently increases, the pressure-sensitive adhesive layer containing the gas generating agent of the present disclosure is excellent in easy peel properties from the adherend. Since the gas generating agent of the present disclosure is likely to localize on the surface of the pressure-sensitive adhesive layer, the generated gas amount on the surface of the pressure-sensitive adhesive layer can be efficiently increased without increasing the content of the gas generating agent. Accordingly, a decrease in the pressure-sensitive adhesion of the pressure-sensitive adhesive layer and clouding of the pressure-sensitive adhesive layer are suppressed. As just described, it is presumed that the gas generating agent of the present disclosure can increase the effect of imparting peel properties to the surface.

The gas generating agent of the present disclosure is an agent which can be decomposed by light irradiation and generate a gas. Since the maximum molar absorption coefficient value at a wavelength of 240 nm to 450 nm is 7000 or more, the gas generating agent of the present disclosure is an agent which can efficiently absorb lights including UV and which can be efficiently decomposed and generate a gas by light irradiation including UV irradiation.

In the general formulae (1) and (2), each A is independently a gas generating moiety represented by the general formula (A-1), (A-2) or (A-3).

In the gas generating moiety represented by the general formula (A-1), by light irradiation, the tetrazole ring is decomposed, and nitrogen gas is generated.

In the gas generating moiety represented by the general formula (A-2), by light irradiation, the —(C═O)—(C═$N_2$)— bond is decomposed into a —(C═C═O)— bond and nitrogen gas, and nitrogen gas is generated.

In the gas generating moiety represented by the general formula (A-3), by light irradiation, the gas generating moiety is decomposed at the azo group moiety, and nitrogen gas is generated.

In the general formula (A-1), the aromatic group as $R^1$, that is, the aromatic group which contains 3 to 20 carbon atoms and which optionally contains a substituent may be appropriately selected so that the compound satisfies the above-specified maximum molar absorption coefficient value.

As the aromatic group which contains 3 to 20 carbon atoms, examples include an aromatic hydrocarbon group and an aromatic heterocyclic group.

As the aromatic hydrocarbon group, examples include an aromatic hydrocarbon group containing 6 to 20 carbon atoms. Preferred is an aromatic hydrocarbon group containing 6 to 12 carbon atoms. As the aromatic hydrocarbon group, examples include a phenyl group, a biphenyl group, a naphthyl group, an anthryl group, a phenanthryl group, a fluorenyl group, a naphthylphenyl group and a pyrenyl group.

As the aromatic heterocyclic group, examples include an aromatic heterocyclic group containing 3 to 20 carbon atoms and at least one of a nitrogen atom, an oxygen atom a sulfur atom. Preferred is an aromatic heterocyclic group containing 3 to 10 carbon atoms. As the aromatic heterocyclic group, examples include a pyrrolyl group, a furyl group, a thienyl group, a pyrazolyl group, an imidazolyl group, an oxazolyl group, an isoxazolyl group, a thiazolyl group, an isothiazolyl group and a carbazole group.

As the substituent the aromatic group optionally contains, examples include, but are not limited to, a halogen atom such as F, Cl and Br, a nitro group, an alkyl group, an alkenyl group, an aralkyl group, an alkoxy group such as a methoxy group, a tertiary amino group such as a diphenylamino group, and an acyl group such as a benzoyl group . The alkyl group, the alkenyl group and the aralkyl group may be an alkyl group containing 1 to 20 carbon atoms, an alkenyl group containing 2 to 20 carbon atoms, and an aralkyl group, respectively, which will be described later. They are preferably an alkyl group containing 1 to 14 carbon atoms, an alkenyl group containing 2 to 14 carbon atoms, and an aralkyl group containing 7 to 14 carbon atoms, respectively. By appropriately selecting the substituent of the aromatic group, the wavelength of absorbed light can be changed, or compatibility with other components can be improved. As the substituent that can shift the wavelength of absorbed light to the long-wavelength side, examples include, but are not limited to, an alkoxy group such as a methoxy group, a diarylamino group such as a diphenylamino group, and an acyl group such as a benzoyl group.

From the point of view that the absorption wavelength range can be expanded and shifted to the long-wavelength side, $R^1$ may be an aromatic hydrocarbon group which contains 6 to 14 carbon atoms and which optionally contains a substituent. Preferred is an aromatic hydrocarbon group which contains 6 to 12 carbon atoms and which optionally contains a substituent, and more preferred is a phenyl group, a naphthyl group or an anthryl group, all of which optionally contain a substituent. In the case of irradiation with light containing UV, a naphthyl group is still more preferred from the viewpoint of high sensitivity and an increase in gas generation efficiency.

When $R^2$ is a hydrocarbon group which contains 1 to 20 carbon atoms and which optionally contains a substituent, as the hydrocarbon group, examples include, but are not limited to, an alkyl group containing 1 to 20 carbon atoms, an alkenyl group containing 2 to 20 carbon atoms, an aralkyl group and an aryl group.

The alkyl group containing 1 to 20 carbon atoms may be linear, branched or cyclic. As the alkyl group, examples include, but are not limited to, a methyl group, an ethyl group, an n-propyl group, an isopropyl group, an n-butyl group, a 2-ethylhexyl group, a cyclopentyl group, a cyclohexyl group, a bornyl group, an isobornyl group, a dicyclopentanyl group, an adamantyl group and a lower alkyl group-substituted adamantyl group.

The alkenyl group containing 2 to 20 carbon atoms may be linear, branched or cyclic. As the alkenyl group, examples include, but are not limited to, a vinyl group, an allyl group and a propenyl group. The position of the double bond of the alkenyl group is not limited. From the viewpoint of reactivity, the alkenyl group preferably has the double bond at the terminal thereof.

The aryl group may be the same as the above-described aromatic hydrocarbon group as $R^1$. As the aryl group, a phenyl group, a biphenyl group, a naphthyl group or the like is preferably used.

As the aralkyl group, examples include, but are not limited to, a benzyl group, a phenethyl group, a naphthylmethyl group and a biphenylmethyl group. The number of the carbon atoms of the aralkyl group is preferably from 7 to 20, and more preferably from 7 to 14.

As the substituent the hydrocarbon group may contain, examples include, but are not limited to, a halogen atom such as F, Cl and Br, and a nitro group.

The substituent of the aromatic ring contained in the aryl group, the aralkyl group or the like may be the above-described alkyl group.

The preferred number of the carbon atoms does not include the number of the carbon atoms of the substituent.

From the viewpoint of solubility in organic solvents, reactivity, and nitrogen content per molecule, $R^2$ is preferably a hydrogen atom or a hydrocarbon group which contains 1 to 6 carbon atoms and which optionally contains a substituent. Each $R^2$ may be a hydrogen atom.

When $R^3$, $R^4$, $R^5$ or $R^7$ is a hydrocarbon group which contains 1 to 20 carbon atoms and which optionally contains a substituent, as the hydrocarbon group, examples include, but are not limited to, those mentioned above as the hydrocarbon group as $R^2$, that is, those mentioned above as the hydrocarbon group which contains 1 to 20 carbon atoms and which optionally contains a substituent.

When $R^6$ is the hydrocarbon group which contains 1 to 5 carbon atoms, as the hydrocarbon group, examples include, but are not limited to, those corresponding to the hydrocarbon group which contains 1 to 5 carbon atoms, among the hydrocarbon groups mentioned above as $R^2$, that is, among the hydrocarbon groups which contain 1 to 20 carbon atoms and which optionally contain a substituent.

The $-L-Q^1$ as $R^4$ may be as described below.

From the viewpoint of solubility in organic solvents and nitrogen content per molecule, each $R^5$ is preferably independently a hydrocarbon group which contains 1 to 20 carbon atoms and which optionally contains a substituent, and more preferably independently a hydrocarbon group which contains 1 to 10 carbon atoms. From the same viewpoint, each $R^7$ is preferably independently a hydrocarbon group which contains 1 to 20 carbon atoms and which optionally contains a substituent, and more preferably independently a hydrocarbon group which contains 1 to 10 carbon atoms.

From the viewpoint of the nitrogen content per molecule of an organic solvent, $R^6$ is preferably a hydrogen atom or a methyl group, and more preferably a hydrogen atom.

From the viewpoint of solubility in organic solvents and nitrogen content per molecule, each $R^3$ is preferably independently a cyano group or a hydrocarbon group which contains 1 to 10 carbon atoms and which optionally contains a substituent, and more preferably independently a hydrocarbon group which contains 1 to 5 carbon atoms. Each $R^3$ may be a methyl group or an ethyl group.

From the viewpoint of solubility in organic solvents and the localization onto the surface of the pressure-sensitive adhesive layer, $R^4$ is preferably the -L-$Q^1$ or a hydrocarbon group which contains 1 to 10 carbon atoms and which optionally contains a substituent, and $R^4$ is more preferably the -L-$Q^1$.

From the viewpoint of the heat resistance and the nitrogen content per molecule, A in the general formulae (1) and (2) is preferably the gas generating moiety represented by the general formula (A-1).

As the gas generating moiety represented by the general formula (A-1), examples include, but are not limited to, the following.

(a-1-1)

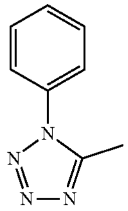

(a-1-2)

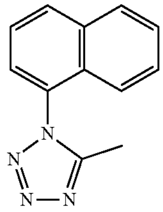

(a-1-3)

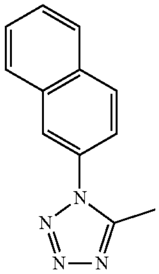

-continued (a-1-4)

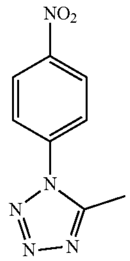

)a-1-5)

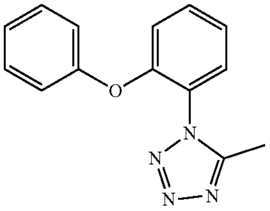

(a-1-6)

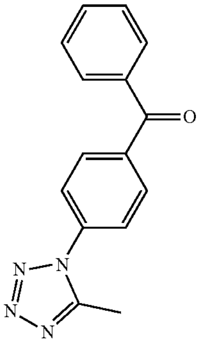

(a-1-7)

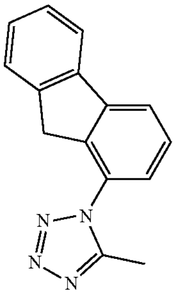

(a-1-8)

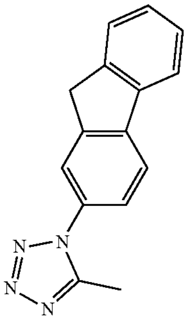

-continued (a-1-9)

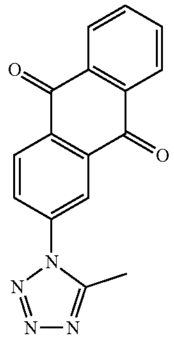

(a-1-10)

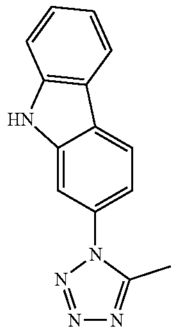

(a-1-11)

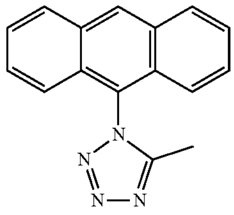

(a-1-12)

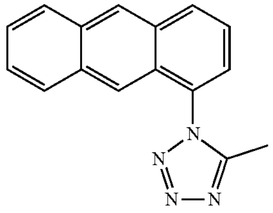

(a-1-13)

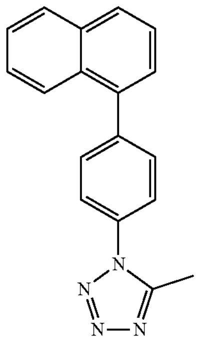

-continued (a-1-14)

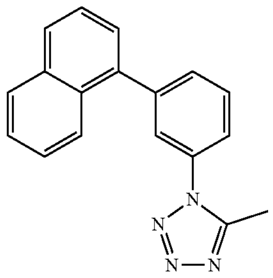

(a-1-15)

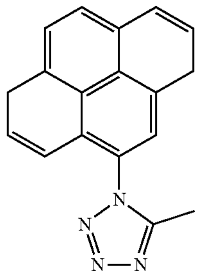

In the general formulae (1) and (2) , $Q^1$ is a monovalent fluorinated aliphatic hydrocarbon group in which a number of carbon atoms to which a fluorine atom is directly bound is from 2 to 8, which optionally contains an ether bond (—O—) in a carbon chain, and which optionally contains a substituent, or $Q^1$ is a monovalent organopolysiloxane group, and $Q^2$ is a divalent fluorinated aliphatic hydrocarbon group in which a number of carbon atoms to which a fluorine atom is directly bound is from 2 to 8 and which optionally contains an ether bond (—O—) in a carbon chain, or $Q^2$ is a divalent organopolysiloxane group.

As the fluorinated aliphatic hydrocarbon group as $Q^1$ and $Q^2$, examples include a linear or branched, saturated or unsaturated fluorinated aliphatic hydrocarbon group.

As long as the number of carbon atoms to which a fluorine atom is directly bound is from 2 to 8, a part of the fluorinated aliphatic hydrocarbon group may contain a carbon atom to which a fluorine atom is not directly bound. For example, when an alkynyl group is contained in the fluorinated aliphatic hydrocarbon group, a carbon atom to which a fluorine atom is not directly bound, is contained.

In the fluorinated aliphatic hydrocarbon group as $Q^1$ and $Q^2$, it is not needed that the carbon atoms to which a fluorine atom is directly bound are not completely substituted with fluorine atoms. A hydrogen atom or a substituent may be contained in a part of the fluorinated aliphatic hydrocarbon group. For example, the substituent may be a reactive group used to be bound to the gas generating moiety, such as a hydroxyl group, an amino group, a carboxy group, a (meth) acryloyloxy group, a vinyl ether group, a phosphoric acid group and an epoxy group.

From the viewpoint of the effect of surface localization, the fluorinated aliphatic hydrocarbon group as $Q^1$ and $Q^2$ preferably contains 4 or more fluorine atoms, and more preferably 6 or more fluorine atoms. The number of the fluorine atoms in the fluorinated aliphatic hydrocarbon group may be 17 or less, or it may be 16 or less.

For the fluorinated aliphatic hydrocarbon group as $Q^1$ and $Q^2$, from the viewpoint of the effect of surface localization, $Q^1$ may be any one of monovalent fluorinated aliphatic hydrocarbon groups represented by the following formulae (Rf-1) to (Rf-5), and $Q^2$ may be a divalent fluorinated aliphatic hydrocarbon group represented by the following formula (Rf-6), for example.

$$—C_nF_{2n+1} \quad (Rf-1)$$

$$—C_nF_{2n}H \quad (Rf-2)$$

$$—C_nF_{2n-1} \quad (Rf-3)$$

$$—C_{n'}F_{2n'-3} \quad (Rf-4)$$

$$—C_nF_{2n}—(OC_{n''}F_{2n''})_m—J^1 \quad (Rf-5)$$

$$—C_nF_{2n}—(OC_{n''}F_{2n''})_m— \quad (Rf-6)$$

in the formulae (Rf-1), (Rf-2) and (Rf-3), each n is independently an integer of 2 to 8;
in the formula (Rf-4), n' is an integer of 4 to 10;
in the formula (Rf-5), n is an integer of 1 to 8; n" is an integer of 0 to 7; m is an integer of 0 to 7; n+n"×m is an integer of 2 to 8; and $J^1$ is a hydrogen atom, a fluorine atom, a hydroxyl group, an amino group, a carboxy group or a (meth)acryloyloxy group; and
in the formula (Rf-6), n is an integer of 0 to 8; n" is an integer of 0 to 4; m is an integer of 0 to 8; and n+n"×m is an integer of 2 to 8.

In the formulae (Rf-1), (Rf-2) and (Rf-3), each n is independently an integer of 2 to 8, and preferably an integer of 4 to 8 from the viewpoint of the effect of surface localization.

In the formula (Rf-4), n' is an integer of 4 to 10, and preferably an integer of 5 to 10 from the viewpoint of the effect of surface localization.

In the formula (Rf-5), n is an integer of 1 to 8; n" is an integer of 0 to 7; m is an integer of 0 to 7; and n+n"×m is an integer of 2 to 8. From the viewpoint of the effect of surface localization, n is preferably an integer of 2 to 8; n" is preferably an integer of 1 to 7; m is preferably an integer of 1 to 7; and n+n"×m is preferably an integer of 3 to 8.

In the formula (Rf-6), n is an integer of 0 to 8; n" is an integer of 0 to 4; m is an integer of 0 to 8; and n+n"×m is an integer of 2 to 8. From the viewpoint of the effect of surface localization, n is preferably an integer of 2 to 8; n" is preferably an integer of 1 to 7; m is an integer of 1 to 7; and n+n"×m is preferably an integer of 3 to 8.

In the formula (Rf-5), $J^1$ is a hydrogen atom, a fluorine atom, a hydroxyl group, an amino group, a carboxy group or a (meth)acryloyloxy group. $J^1$ is preferably a hydrogen atom or a fluorine atom, and more preferably a fluorine atom. $J^1$ may be a hydroxyl group, an amino group, a carboxy group or a (meth)acryloyloxy group. When $J^1$ contains such a reactive group, it may be used to bind the gas generating agent and another component contained in the pressure-sensitive adhesive composition.

In the preparation of the compound of the general formula (2), even when the gas generating moiety is not introduced into both terminals thereof and the gas generating moiety is introduced into only one terminal, the compound may have the structure of the general formula (1) and may contain a reactive group such as a hydroxyl group, an amino group, a carboxy group and a (meth)acryloyloxy group in the other terminal.

$Q^1$ is preferably any one of monovalent fluorinated aliphatic hydrocarbon groups represented by the formulae (Rf-1) and (Rf-5), more preferably a monovalent fluorinated aliphatic hydrocarbon group represented by the formula (Rf-1) or (Rf-5), and still more preferably a monovalent fluorinated aliphatic hydrocarbon group represented by the formula (Rf-1).

The organopolysiloxane group as $Q^1$ and $Q^2$ is a group which contains a siloxane bond $—(O—Si)_a—$ (where a is a repeating number) in the main chain and which contains a hydrocarbon group in part of the side chains.

For the organopolysiloxane group as $Q^1$ and $Q^2$, from the viewpoint of the effect of surface localization, $Q^1$ may be a monovalent organopolysiloxane group represented by the following formula (Si-1), and $Q^2$ may be a divalent organopolysiloxane group represented by the following formula (Si-2), for example.

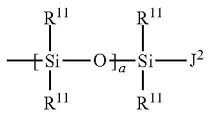
(Si-1)

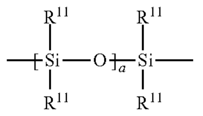
(Si-2)

In the formulae (Si-1) and (Si-2), each $R^{11}$ is independently a monovalent hydrocarbon group which contains 1 to 20 carbon atoms and which optionally contains a substituent, a hydrogen atom, a hydroxyl group, an alkoxy group which contains 1 to 20 carbon atoms, or a group represented by the following formula (Si-3); $J^2$ is a monovalent hydrocarbon group which contains 1 to 20 carbon atoms and which optionally contains a substituent, a hydrogen atom, a hydroxyl group, an alkoxy group which contains 1 to 20 carbon atoms, an amino group, a carboxy group or a (meth)acryloyloxy group; and each a is independently a number of 1 to 100; and

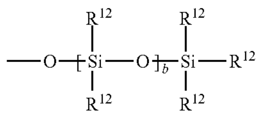
(Si-3)

in the formula (Si-3), each $R^{12}$ is independently a monovalent hydrocarbon group which contains 1 to 20 carbon atoms and which optionally contains a substituent, a hydrogen atom, a hydroxyl group or an alkoxy group which contains 1 to 20 carbon atoms, and b is a number of 0 to 100.

When $R^{11}$ or $R^{12}$ is a monovalent hydrocarbon group which contains 1 to 20 carbon atoms and which optionally contains a substituent, the monovalent hydrocarbon group may be the same as the above-mentioned hydrocarbon group as $R^2$, that is, the hydrocarbon group which contains 1 to 20 carbon atoms and which optionally contains a substituent. The monovalent hydrocarbon group as $R^{11}$ and $R^{12}$, that is , the monovalent hydrocarbon group which contains 1 to 20 carbon atoms and which optionally contains a substituent is preferably a hydrocarbon group which contains 1 to 10 carbon atoms and which optionally contains a substituent. As the hydrocarbon group which contains 1 to 10 carbon atoms and which optionally contains a substituent, examples include, but are not limited to, an alkyl group such as a methyl group, an ethyl group, a propyl group and a butyl group, a cycloalkyl group such as a cyclohexyl group, an aryl group such as a phenyl group and a tolyl group, an aralkyl group such as a benzyl group and a phenethyl group, and the above-mentioned groups in each of which a part or all of hydrogen atoms bound to the carbon atom(s) of the group are substituted with hydroxy groups, cyano groups, halogen atoms or the like, such as a hydroxypropyl group, a cyanoethyl group, a 1-chloropropyl group and a 3,3,3-trifluoropropyl group.

When $R^{11}$ or $R^{12}$ is an alkoxy group which contains 1 to 20 carbon atoms, the alkoxy group is preferably an alkoxy group which contains 1 to 10 carbon atoms, such as a methoxy group, an ethoxy group, a propoxy group and a butoxy group.

From the viewpoint of the solubility in organic solvents, $R^{11}$ and $R^{12}$ are preferably an alkyl group which contains 1 to 10 carbon atoms, an aryl group or a group represented by the formula (Si-3), and more preferably an alkyl group which contains 1 to 5 carbon atoms. $R^{12}$ is preferably an alkyl group which contains 1 to 10 carbon atoms or an aryl group, and more preferably an alkyl group which contains 1 to 5 carbon atoms.

$J^2$ is a monovalent hydrocarbon group which contains 1 to 20 carbon atoms and which optionally contains a substituent, a hydrogen atom, a hydroxyl group, an alkoxy group which contains 1 to 20 carbon atoms, an amino group, a carboxy group or a (meth)acryloyloxy group. $J^2$ is preferably a monovalent hydrocarbon group which contains 1 to 20 carbon atoms and which optionally contains a substituent, a hydrogen atom or an alkoxy group which contains 1 to 20 carbon atoms, or $J^2$ may be a hydroxyl group, an amino group, a carboxy group or a (meth)acryloyloxy group. When $J^2$ contains such a reactive group, it may be used to bind the gas generating agent and another component contained in the pressure-sensitive adhesive composition.

In the preparation of the compound of the general formula (2), even when the gas generating moiety is not introduced into both terminals thereof and the gas generating moiety is introduced into only one terminal, the compound may have the structure of the general formula (1) and may contain a reactive group such as a hydroxyl group, an amino group, a carboxy group and a (meth)acryloyloxy group in the other terminal.

In the formulae (Si-1) and (Si-2), a is a number of 1 to 100. Since a may have a distribution, it may be an average value. From the viewpoint of the nitrogen content per molecule, a is preferably a number of 1 to 50, more preferably a number of 5 to 45, and still more preferably a number of 10 to 40.

In the formula (Si-3), b is a number of 0 to 100. Since b may have a distribution, it may be an average value. More specifically, b is preferably a number of 0 to 40, and more preferably a number of 0 to 30.

When the gas generating agent is used in the semiconductor field and the display field, since there is a low possibility of contamination, $Q^1$ is preferably a monovalent fluorinated aliphatic hydrocarbon group in which the number of carbon atoms to which a fluorine atom is directly bound is from 2 to 8, which optionally contains an ether bond (—O—) in a carbon chain, and which optionally contains a substituent, and $Q^2$ is preferably a divalent fluorinated aliphatic hydrocarbon group in which the number of carbon atoms to which a fluorine atom is directly bound is from 2 to 8 and which optionally contains an ether bond (—O—) in a carbon chain.

In the general formulae (1) and (2), each L is independently a direct bond or a divalent linking group. In the general formulae (1) and (2), L is a moiety that binds the gas generating moiety and the above-specified fluorinated aliphatic hydrocarbon group or organopolysiloxane group. L is not particularly limited, as long as it is a binding moiety that can bind the above-specified fluorinated aliphatic hydrocarbon group or organopolysiloxane group to the gas generating moiety.

The direct bond means that L do not contain an atom, that is, the carbon atom of A in the general formulae (1) and (2) and the carbon or silicon atom of $Q^1$ or $Q^2$ bind to each other without another atom.

In the general formulae (1) and (2), for example, each L may be independently a direct bond, $—SCH_2CH_2COO—$, $—SCH_2CH(CH_3)COO—$, $—SCH_2CH(OH)CH_2—$, $—OCH_2CH(OH)CH_2—$, $—SCH (CH_3)O—$, $—OCH (CH_3) O—$, —COO—, —CONH—, —COS—, $—SO_2NH—$, or a hydrocarbon group which contains 1 to 22 carbon atoms, which optionally contains at least one selected from the group consisting of —O— and —S—, and which is optionally substituted by a hydroxyl group, or a combination thereof. In L, the direction of the bond may be any direction. That is, when L is $—SCH_2CH_2COO—$, it encompasses the case where S binds to the carbon atom of A and O binds to the carbon or silicon atom of $Q^1$ or $Q^2$, and the case where S binds to the carbon or silicon atom of $Q^1$ or $Q^2$ and O binds to the carbon atom of A.

As the hydrocarbon group which contains 1 to 22 carbon atoms, examples include, but are not limited to, an alkylene group such as a methylene group, an ethylene group, a propylene group (e.g., a trimethylene group, a methylethylene group), a butylene group (e.g., a tetramethylene group, a methylpropylene group), a pentamethylene group, a hexamethylene group, an octamethylene group and a cyclohexylene group, an arylene group such as a phenylene group, and combinations of two or more kinds thereof (e.g., an alkylene-arylene group).

As the combination as L in the general formulae (1) and (2), examples include, but are not limited to, the following:

(L1): $—SCH_2CH_2COO—(C_jH_{2j})—$, (L2) : $—SCH_2CH_2COO—(C_jH_{2j})—O— (C_jH_{2j})—$, (L3) : $—SCH_2CH_2COO—(C_jH_{2j})—NHCO—(C_kH_{2k})—$, (L4) : $—SCH_2CH_2CO—OCH_2CH(OH)CH_2O—(C_jH_{2j})—$, (L5) : $—SCH_2CH_2CO—OCH_2CH(OH)—(C_jH_{2j})—$, (L6) : $—SCH_2CH_2COO—(C_jH_{2j})—NHCO—CH\{CH_2O—(C_kH_{2k})—Rf\}—CH_2O—(C_1H_{21})—$, (L7) : $—SCH_2CH_2COO—CH\{CH_2O—(C_jH_{2j})—Rf\}—CH_2O—(C_kH_{2k})—$, (L8) : $—SCH_2CH_2COO—(C_jH_{2j})—N (C_kH_{2k+1})SO_2—$ (L9) : $—SCH_2CH_2CON (C_jH_{2j+1})—(C_kH_{2k})—$, (L10) : $—SCH_2CH_2COO—(C_jH_{2j})—N(C_kH_{2k+1})CO—$, and (L11): $—OCH(CH_3)O—(C_jH_{2j+1})—$(where each j is independently an integer of 1 to 8; each k is independently an integer of 1 to 8; each 1 is independently an integer of 1 to 8; and Rf is any one of monovalent fluorinated aliphatic hydrocarbon groups represented by the general formulae (Rf-1) to (Rf-3).

Also, each j is preferably independently an integer of 2 to 6, and more preferably independently an integer of 2 to 4; each k is preferably independently an integer of 2 to 6, and more preferably independently an integer of 2 to 4; and each 1 is preferably independently an integer of 2 to 6, and more preferably independently an integer of 2 to 4.

From the viewpoint of foamability in the UV range, the gas generating agent of the present disclosure is preferably a gas generating agent which generates a gas by light irradiation, which has the maximum molar absorption coefficient value of 7000 or more at a wavelength of 240 nm to 450 nm, and which is represented by at least one of the following general formulae (1-1) and (2-1):

(1-1)

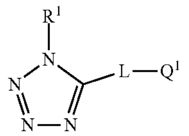

(2-1)

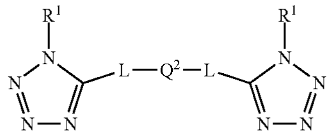

in the general formulae (1-1) and (2-1), each $R^1$ is independently the same as $R^1$ in the general formulae (1) and (2); each L is independently the same as L in the general formulae (1) and (2); each $Q^1$ is independently the same as $Q^1$ in the general formulae (1) and (2); and each $Q^2$ is independently the same as $Q^2$ in the general formulae (1) and (2).

As the compound represented by the general formula (1-1), examples include, but are not limited to, the following compounds. For example, the compound represented by the general formula (1-1) may be a combination of any one of the above-described (a-1-1) to (a-1-15) as A, any one of the above-described (L1) to (L11) as L, and any one of the above-described (Rf-1) to (Rf-5) and (Si-3) as $Q^1$.

TABLE 1

| Compound | A | L | $Q^1$ |
|---|---|---|---|
| (1-1-1) | (a-1-1) | (L1) j = 2 | (Rf-1) n = 4 |
| (1-1-2) | (a-1-1) | (L1) j = 2 | (Rf-1) n = 5 |
| (1-1-3) | (a-1-1) | (L1) j = 2 | (Rf-1) n = 6 |
| (1-1-4) | (a-1-1) | (L1) j = 2 | (Rf-1) n = 7 |
| (1-1-5) | (a-1-1) | (L1) j = 2 | (Rf-1) n = 8 |
| (1-1-6) | (a-1-1) | (L5) j = 1 | (Rf-1) n = 4 |
| (1-1-7) | (a-1-1) | (L5) j = 1 | (Rf-1) n = 6 |
| (1-1-8) | (a-1-1) | (L11) j = 2 | (Rf-1) n = 4 |
| (1-1-9) | (a-1-1) | (L11) j = 2 | (Rf-1) n = 6 |
| (1-1-10) | (a-1-1) | (L3) j = 1 | (Rf-1) n = 4 |
| (1-1-11) | (a-1-1) | (L3) j = 1 | (Rf-1) n = 6 |
| (1-1-12) | (a-1-1) | (L3) j = 1 | (Rf-1) n = 8 |
| (1-1-13) | (a-1-1) | (L3) j = 1 | (Rf-5) n, n'' = 1, m = 2 |
| (1-1-14) | (a-1-1) | (L3) j = 1 | (Rf-5) n, n'' = 1, m = 3 |
| (1-1-15) | (a-1-1) | (L3) j = 1 | (Rf-5) n, n'' = 1, m = 4 |
| (1-1-16) | (a-1-1) | (L3) j = 1 | (Rf-5) n, n'' = 3, m = 1 |
| (1-1-17) | (a-1-2) | (L1) j = 2 | (Rf-1) n = 4 |
| (1-1-18) | (a-1-2) | (L1) j = 2 | (Rf-1) n = 5 |
| (1-1-19) | (a-1-2) | (L1) j = 2 | (Rf-1) n = 6 |
| (1-1-20) | (a-1-2) | (L5) j = 1 | (Rf-1) n = 4 |
| (1-1-21) | (a-1-2) | (L5) j = 1 | (Rf-1) n = 6 |
| (1-1-22) | (a-1-2) | (L11) j = 2 | (Rf-1) n = 4 |
| (1-1-23) | (a-1-2) | (L11) j = 2 | (Rf-1) n = 6 |
| (1-1-24) | (a-1-2) | (L3) j = 1 | (Rf-1) n = 4 |
| (1-1-25) | (a-1-2) | (L3) j = 1 | (Rf-1) n = 6 |
| (1-1-26) | (a-1-2) | (L3) j = 1 | (Rf-1) n = 8 |
| (1-1-27) | (a-1-2) | (L3) j = 1 | (Rf-5) n, n'' = 1, m = 2 |
| (1-1-28) | (a-1-2) | (L3) j = 1 | (Rf-5) n, n'' = 1, m = 3 |
| (1-1-29) | (a-1-2) | (L3) j = 1 | (Rf-5) n, n'' = 1, m = 4 |
| (1-1-30) | (a-1-2) | (L3) j = 1 | (Rf-5) n, n'' = 3, m = 1 |

As the compound represented by the general formula (2-1), examples include, but are not limited to, the following compounds. For example, the compound represented by the general formula (2-1) may be a combination of any one of the above-described (a-1-1) to (a-1-15) as A, any one of the above-described (L1) to (L11) as L, and any one of the above-described (Rf-6) and (Si-2) as $Q^2$.

TABLE 2

| Compound | A | L | $Q^2$ | L | A |
|---|---|---|---|---|---|
| (2-1-1) | (a-1-1) | (L1) j = 2 | (Si-2) $R^{11}$: Methyl, a = 25 on average | (L1) j = 2 | (a-1-1) |
| (2-1-2) | (a-1-2) | (L1) j = 2 | (Si-2) $R^{11}$: Methyl, a = 25 on average | (L1) j = 2 | (a-1-2) |
| (2-1-3) | (a-1-1) | (L1) j = 1 | (Rf-6) n = 2, n'' = 0, m = 0 | (L1) j = 1 | (a-1-1) |
| (2-1-4) | (a-1-2) | (L1) j = 1 | (Rf-6) n = 2, n'' = 0, m = 0 | (L1) j = 1 | (a-1-2) |
| (2-1-5) | (a-1-1) | (L1) j = 1 | (Rf-6) n = 4, n'' = 0, m = 0 | (L1) j = 1 | (a-1-1) |
| (2-1-6) | (a-1-2) | (L1) j = 1 | (Rf-6) n = 4, n'' = 0, m = 0 | (L1) j = 1 | (a-1-2) |
| (2-1-7) | (a-1-1) | (L1) j = 1 | (Rf-6) n = 1, n'' = 1, m = 1 | (L1) j = 1 | (a-1-1) |
| (2-1-8) | (a-1-1) | (L1) j = 1 | (Rf-6) n = 1, n'' = 1, m = 2 | (L1) j = 1 | (a-1-1) |
| (2-1-9) | (a-1-1) | (L1) j = 1 | (Rf-6) n = 1, n'' = 1, m = 3 | (L1) j = 1 | (a-1-1) |
| (2-1-10) | (a-1-1) | (L1) j = 1 | (Rf-6) n = 1, n'' = 1, m = 4 | (L1) j = 1 | (a-1-1) |
| (2-1-11) | (a-1-1) | (L1) j = 1 | (Rf-6) n = 3, n'' = 3, m = 1 | (L1) j = 1 | (a-1-1) |
| (2-1-12) | (a-1-1) | (L3) j = 1 | (Rf-6) n = 2, n'' = 0, m = 0 | (L3) j = 1 | (a-1-1) |
| (2-1-13) | (a-1-2) | (L3) j = 1 | (Rf-6) n = 2, n'' = 0, m = 0 | (L3) j = 1 | (a-1-2) |
| (2-1-14) | (a-1-1) | (L3) j = 1 | (Rf-6) n = 4, n'' = 0, m = 0 | (L3) j = 1 | (a-1-1) |
| (2-1-15) | (a-1-2) | (L3) j = 1 | (Rf-6) n = 4, n'' = 0, m = 0 | (L3) j = 1 | (a-1-2) |
| (2-1-16) | (a-1-1) | (L3) j = 1 | (Rf-6) n = 1, n'' = 1, m = 1 | (L3) j = 1 | (a-1-1) |
| (2-1-17) | (a-1-1) | (L3) j = 1 | (Rf-6) n = 1, n'' = 1, m = 2 | (L3) j = 1 | (a-1-1) |
| (2-1-18) | (a-1-1) | (L3) j = 1 | (Rf-6) n = 1, n'' = 1, m = 3 | (L3) j = 1 | (a-1-1) |
| (2-1-19) | (a-1-1) | (L3) j = 1 | (Rf-6) n = 1, n'' = 1, m = 4 | (L3) j = 1 | (a-1-1) |
| (2-1-20) | (a-1-1) | (L3) j = 1 | (Rf-6) n = 3, n'' = 3, m = 1 | (L3) j = 1 | (a-1-1) |

[Properties of Gas Generating Agent]

Since the maximum molar absorption coefficient value at a wavelength of 240 nm to 450 nm is 7000 or more, the gas generating agent of the present disclosure can efficiently generate a gas by light irradiation. From the viewpoint of efficiently generating a gas and improving easy peel properties, the maximum molar absorption coefficient value of the gas generating agent of the present disclosure at a wavelength of 240 nm to 450 nm, is preferably 8000 or more, and more preferably 9000 or more.

The molar absorption coefficient of the DESCRIPTION is a value obtained as follows: 0.1 mM of the gas generating agent is dissolved in ethyl acetate; an absorption spectrum in a wavelength range of from 230 nm to 800 nm is measured by use of a ultraviolet-visible spectrophotometer (e.g., ultraviolet-visible spectrophotometer UV2700 manufactured by Shimadzu Corporation); using the absorbance in the obtained absorption spectrum, the molar absorption coefficient is calculated by the following formula:

$$\varepsilon = A/c \times d$$

(where ε is molar absorption coefficient; A is absorbance; c is mol concentration; and d is cell thickness).

When 0.1 mM of the gas generating agent cannot be dissolved in ethyl acetate, a solvent that has no problem with the reproducibility of the molar absorption coefficient of the gas generating agent is appropriately selected; 0.1 mM of the gas generating agent is dissolved in the solvent; and the molar absorption coefficient is obtained in the same manner as above. As the solvent that has no problem with the reproducibility of the molar absorption coefficient of the gas generating agent, examples include an organic solvent which does not have an absorption spectrum in a wavelength range of from 230 nm to 800 nm and which is not reactive with the gas generating agent, such as acetonitrile and dichloromethane.

In the DESCRIPTION, when the maximum molar absorption coefficient value at a wavelength of 240 nm to 450 nm is 7000 or more, it means that no peak may be present between a wavelength of 240 nm and a wavelength of 450 nm, as long as the value of the molar absorption coefficient at a wavelength between 240 nm and 450 nm is 7000 or more.

The molecular weight or mass average molecular weight Mw of the gas generating agent of the present disclosure, is not particularly limited. From the viewpoint of the content of nitrogen atoms per molecule, it is preferably from 200 to 2000, and more preferably from 300 to 1000.

The molecular weight of the gas generating agent can be obtained by liquid chromatography mass spectrometry (LC-MS).

When the gas generating agent contains an organopolysiloxane group, it may be specified by the mass average molecular weight. The mass average molecular weight can be obtained as a standard polystyrene equivalent molecular weight by gel permeation chromatography (GPC).

[Method for Producing Gas Generating Agent]

The method for producing the gas generating agent of the present disclosure is not particularly limited. For example, the gas generating agent of the present disclosure can be obtained by reacting and binding the gas generating moiety containing a reactive group with a compound containing a fluorinated aliphatic hydrocarbon group or organopolysiloxane group and a reactive group which is reactive with the reactive group of the gas generating moiety to form a bond.

As the combination of the reactive groups, examples include, but are not limited to, a combination of a thiol group and a (meth)acryloyloxy group, a combination of a thiol group and an epoxy group, a combination of a thiol group and a vinyl ether group, a combination of a hydroxyl group and a vinyl ether group, a combination of a hydroxyl group and an epoxy group, a combination of a hydroxyl group and an isocyanate group, a combination of an amino group and a sulfonyl chloride group, and a combination of a carboxy group and an epoxy group. In each combination, one may a gas generating moiety-side reactive group, and the other may be a reactive group on the side of the compound containing the fluorinated aliphatic hydrocarbon group or organopolysiloxane group.

The gas generating moiety containing a reactive group can be synthesized in reference to, for example, Russian Journal of General Chemistry (2017), 87(4), pp. 731-738. For example, by reacting an isothiocyanate derivative (R—N═C═S where R is an aromatic group which contains 3 to 20 carbon atoms) with sodium azide, a tetrazole compound substituted with a thiol group and R (an aromatic group which contains 3 to 20 carbon atoms) are substituted, can be synthesized. Also, a naphthoquinonediazide compound containing a sulfonyl chloride group can be synthesized in reference to JP-A No. S59-196860. Also an azo-based compound containing a carboxyl group can be synthesized by reacting sodium cyanide, 4-oxopentanoic acid and hydrazine monohydrate in reference to Shandong Huagong, Volume: 37, Issue: 3, Pages: 7-9, Journal, 2008. Also, a commercially-available product may be appropriately selected and used as the gas generating moiety containing a reactive group.

Also, as for the compound containing the fluorinated aliphatic hydrocarbon group or organopolysiloxane group and the reactive group, a compound containing an organopolysiloxane group can be synthesized by, for example, reacting a naphthoquinonediazide compound containing a sulfonyl chloride group with an organopolysiloxane compound containing an amino group, in reference to Patent No. 6137289 or Chemistry Select, Volume: 3, Issue: 15, Pages: 4129-4132, Journal, 2018. Also, a compound containing a fluorinated aliphatic hydrocarbon group can be synthesized by reacting a vinyl ether group containing a fluorinated aliphatic hydrocarbon group with an azo-based compound containing a carboxyl group , in reference to Macromolecules, Volume: 37, Issue: 18, Pages: 6673-6675, Journal, 2004. Also, a commercially-available product may be appropriately selected and used as the compound containing the fluorinated aliphatic hydrocarbon group or organopolysiloxane group and the reactive group.

[Applications of Gas Generating Agent]

Since the gas generating agent of the present disclosure contains the above-specified fluorinated aliphatic hydrocarbon group or organopolysiloxane group in the gas generating moiety having the above-specified structure, the gas generating agent is likely to localize on the surface. Accordingly, as will be described later, the gas generating agent of the present disclosure is preferably applied to pressure-sensitive adhesive materials directed to high adhesion and easy peel to improve easy peel properties.

B. Pressure-Sensitive Adhesive Composition

The pressure-sensitive adhesive composition of one embodiment of the present disclosure contains a pressure-sensitive adhesive component and the gas generating agent of the present disclosure.

Since the pressure-sensitive adhesive composition of one embodiment of the present disclosure contains the gas generating agent of the present disclosure, the generated gas amount on the pressure-sensitive adhesive layer surface is efficiently increased by the action of the gas generating agent that is, as described above, likely to localize on the surface. Accordingly, a pressure-sensitive adhesive layer having the following properties can be formed: while having excellent pressure-sensitive adhesion in a use where pressure-sensitive adhesion is required, it shows excellent easy peel properties from an adherend when pressure-sensitive adhesion is no longer required, such as when peeling the pressure-sensitive adhesive layer from the adherend, is no longer required.

[Pressure-Sensitive Adhesive Component]

The pressure-sensitive adhesive component is not particularly limited, and it may be a non-photocurable or photocurable pressure-sensitive adhesive component.

When the pressure-sensitive adhesive component is a non-photocurable pressure-sensitive adhesive component, gas is generated from the gas generating agent of the present disclosure by light irradiation; peel stress is produced by the generated gas; and the contact area with the adherend is decreased for peel-off.

When the pressure-sensitive adhesive component is a photocurable pressure-sensitive adhesive component, peeling can be more easily achieved by the synergy between a decrease in the contact area with the adherend, which is due to the generation of a gas from the gas generating agent of the present disclosure by light irradiation, and a decrease in the pressure-sensitive adhesion of the pressure-sensitive adhesive component itself, which is due to photocuring of the pressure-sensitive adhesive component. Accordingly, the pressure-sensitive adhesive component is preferably photocurable.

As the photocurable, examples include, but are not limited to, a pressure-sensitive adhesive component which contains a photocurable component and a photoinitiator while containing a pressure-sensitive adhesive.

As the photocurable pressure-sensitive adhesive component used in the pressure-sensitive adhesive composition of one embodiment of the present disclosure, examples include, but are not limited to, the following cases: (i) a composition containing a pressure-sensitive adhesive, a photocurable polyfunctional compound and a photoinitiator, and (ii) a composition containing a photoinitiator and a pressure-sensitive adhesive which contains two or more photocurable functional groups per molecule. From the viewpoint of ease of pressure-sensitive adhesion control, the photocurable pressure-sensitive adhesive component is preferably (i) a composition containing a pressure-sensitive adhesive, a photocurable polyfunctional compound and a photoinitiator. In the case (i), the pressure-sensitive adhesive may contain a photocurable functional group.

(Pressure-Sensitive Adhesive)

As the pressure-sensitive adhesive, examples include, but are not limited to, a rubber-based pressure-sensitive adhesive, an acryl-based pressure-sensitive adhesive, a vinyl alkyl ether-based pressure-sensitive adhesive, a silicone-based pressure-sensitive adhesive, a polyester-based pressure-sensitive adhesive, a polyamide-based pressure-sensitive adhesive, a urethane-based pressure-sensitive adhesive and a styrene-diene block copolymer-based pressure-sensitive adhesive.

From the viewpoint of compatibility with the photocurable component and pressure-sensitive adhesion control, the pressure-sensitive adhesive is preferably a (meth)acrylic acid ester-based polymer called "acryl-based pressure-sensitive adhesive".

As the (meth)acrylic acid ester-based polymer, a (meth) acrylic acid ester-based copolymer, which is used as an acryl-based pressure-sensitive adhesive, obtained by copolymerizing (meth)acrylic acid alkyl ester monomers in which the number of the carbon atoms of a linear or branched alkyl group is 1 or more and 20 or less, or copolymerizing such a monomer and another monomer, is preferably used.

The (meth)acrylic acid ester-based polymer is preferably a (meth)acrylic acid ester-based copolymer containing a constitutional unit derived from a (meth)acrylic acid alkyl ester monomer in which the number of the carbon atoms of a linear or branched alkyl group is 1 or more and 20 or less and a constitutional unit derived from a crosslinkable group-containing monomer. By utilizing the crosslinkable group introduced into the molecule of the (meth)acrylic acid ester polymer, the (meth)acrylic acid ester-based copolymer enables crosslinking with the below-described thermal crosslinking agent and so on, can increase the cohesion of the pressure-sensitive adhesive composition, and can obtain the pressure-sensitive adhesive layer with good balance between durability under a given environment and easy peel properties.

As the (meth)acrylic acid alkyl ester monomer in which the number of the carbon atoms of the linear or branched alkyl group is 1 or more and 20 or less, examples include, but are not limited to, methyl (meth)acrylate, ethyl (meth) acrylate, propyl (meth)acrylate, n-butyl (meth) acrylate, n-pentyl (meth)acrylate, n-hexyl (meth) acrylate, 2-ethylhexyl (meth)acrylate, n-octyl (meth)acrylate, isooctyl (meth)acrylate, n-nonyl (meth)acrylate, isononyl (meth) acrylate, n-decyl (meth)acrylate, isodecyl (meth) acrylate, n-dodecyl (meth) acrylate, n-tridecyl (meth)acrylate, n-tetradecyl (meth) acrylate, n-hexadecyl (meth)acrylate, n-octadecyl (meth)acrylate, and combinations thereof. From the viewpoint of exerting wettability and pressure-sensitive adhesion to the adherend, a (meth)acrylic acid alkyl ester which contains a linear branched alkyl group containing 4 to 14 carbon atoms, is preferred, and a (meth)acrylic acid alkyl ester which contains a linear or branched alkyl group containing 7 to 13 carbon atoms, is more preferred.

As the crosslinkable group of the crosslinkable group-containing monomer used in the (meth)acrylic acid ester-based polymer, examples include, but are not limited to, a hydroxyl group, an epoxy group, an isocyanate group, a carboxy group and an amino group.

From the viewpoint of stability during the polymerization and storage of the polymer, the polymer preferably contains a constitutional unit derived from a monomer which contains one or more kinds selected from the group consisting of a hydroxyl group, an epoxy group, a carboxy group and an amino group. From the viewpoint of obtaining high stability and imparting excellent reactivity to the thermal crosslinking agent, the polymer more preferably contains a constitutional unit derived from a hydroxyl group-containing monomer.

As the monomer that can induce the constitutional unit derived from the hydroxyl group-containing monomer, examples include, but are not limited to, 2-hydroxyethyl (meth)acrylate, 2-hydroxypropyl (meth)acrylate and glycerin mono(meth)acrylate.

As the monomer that can induce the constitutional unit derived from the epoxy group-containing monomer, examples include, but are not limited to, glycidyl (meth) acrylate and 3,4-epoxycyclohexylmethyl(meth)acrylate.

As the monomer that can induce the constitutional unit derived from the isocyanate group-containing monomer, examples include, but are not limited to, 2-(meth)acryloyloxyethyl isocyanate and alkylene oxide adducts thereof.

As the monomer that can induce the constitutional unit derived from the amino group-containing monomer, examples include, but are not limited to, ethylaminoethyl (meth)acrylate and dimethylaminoethyl (meth) acrylate.

As the monomer that can induce the constitutional unit derived from the carboxy group-containing monomer, examples include, but are not limited to, (meth)acrylic acid, vinylbenzoic acid, maleic acid and ω-carboxy-polycaprolactone mono(meth)acrylate.

The (meth)acrylic acid ester-based polymer may further contain a photocurable functional group in a side chain thereof.

The photocurable functional group preferably contains an ethylenically unsaturated bond. Such a photocurable functional group is preferably a (meth)acryloyl group, a vinyl group, an allyl group or the like.

To introduce the photocurable functional group into a side chain of the (meth)acrylic acid ester-based polymer, a conventionally-known production method may be appropriately selected and used.

For example, the photocurable functional group can be added by reacting a (meth)acrylic acid ester-based polymer containing a carboxy group with glycidyl (meth)acrylate, reacting a (meth)acrylic acid ester-based polymer containing an isocyanate group with hydroxyethyl (meth)acrylate, or reacting a (meth)acrylic acid ester-based polymer containing a hydroxyl group with 2-isocyanatoethyl (meth)acrylate.

The (meth)acrylic acid ester-based polymer may contain a constitutional unit derived from another monomer, to the extent that can function as an acryl-based pressure-sensitive adhesive.

As another monomer, for example, a rigid monomer can be used, such as cyclohexyl methacrylate, benzyl methacrylate and adamantyl methacrylate.

A main component constituting the (meth)acrylic acid ester-based polymer is a (meth)acrylic acid ester monomer. Accordingly, with respect to the total monomer component (100% by mass), the content of the monomer is preferably 50% by mass or more.

With respect to the total monomer component, the content of the (meth)acrylic acid alkyl ester monomer is 50% by mass or more, for example. It may be 60% by mass or more, 80% by mass or more, or 90% by mass or more. On the other hand, with respect to the total monomer component, the content of the (meth)acrylic acid alkyl ester monomer is 99.5% by mass or less, for example. It may be 99% by mass or less, or it may be 98% by mass or less.

From the viewpoint of a balance between pressure-sensitive adhesion and peel adhesion, the content of the crosslinkable group-containing monomer may be appropriately selected. For example, with respect to the total monomer component, the content of the crosslinkable group-containing monomer may be 0.5% by mass or more, for example. It may be 1% by mass or more, or it may be 2% by mass or more. On the other hand, with respect to the total monomer component, the content of the crosslinkable group-containing monomer is 15% by mass or less, for example. It may be 13% by mass or less, or it may be 10% by mass or less.

From the viewpoint of performance needed to be imparted and a balance between pressure-sensitive adhesion and peel adhesion, the content of another monomer in the (meth) acrylic acid ester-based polymer may be appropriately selected. For example, it is 0% by mass or more and 49.5% by mass or less. It may be 39% by mass or less, or it may be 18% by mass or less.

From the viewpoint of a good balance between pressure-sensitive adhesion and peel adhesion, the mass average molecular weight of the (meth)acrylic acid ester-based polymer is preferably from 100,000 to 5,000,000, more preferably from 200,000 to 4,000,000, still more preferably from 300,000 to 3,000,000, and even more preferably from 400,000 to 1,000,000. When the mass average molecular weight is smaller than 100,000, the cohesion may be small, and there is a possibility of adhesive residue on the adherend surface after peeling, or there is a possibility of failing to obtain the pressure-sensitive adhesive effect. When the mass average molecular weight exceeds 5,000,000, the wettability of the adherend surface after peeling off the pressure-sensitive adhesive layer may be insufficient.

The mass average molecular weight of the (meth)acrylic acid ester-based polymer can be obtained as a standard polystyrene equivalent molecular weight by gel permeation chromatography (GPC).

As the (meth)acrylic acid ester-based polymer, a commercially-available acryl-based pressure-sensitive adhesive may be used. For example, any of the following products can be preferably used: SK-DYNE 2971 (manufactured by Soken Chemical & Engineering Co., Ltd.), SK-DYNE 2975 (manufactured by Soken Chemical & Engineering Co., Ltd.), SK-DYNE 1811L (manufactured by Soken Chemical & Engineering Co., Ltd.), SK-DYNE 2950 (manufactured by Soken Chemical & Engineering Co., Ltd.), SK-DYNE 2094 (manufactured by Soken Chemical & Engineering Co., Ltd.) and ORIBAIN EG-654 (manufactured by Toyochem Co., Ltd.)

The above pressure-sensitive adhesives can be used alone or in combination of two or more.

From the viewpoint of pressure-sensitive adhesion effect, with respect to the solid content of the pressure-sensitive adhesive composition, the content of the pressure-sensitive adhesive may be 20% by mass or more, or it may be 30% by mass or more. From the viewpoint of removability of the pressure-sensitive adhesive layer, with respect to the solid content of the pressure-sensitive adhesive composition, the content of the pressure-sensitive adhesive may be 80% by mass or less, or it may be 70% by mass or less.

In the DESCRIPTION, the solid content means all components other than solvents.

(Photocurable Polyfunctional Compound)

As the photocurable component, a photocurable polyfunctional compound is preferably contained. The photocurable polyfunctional compound is a monomer, oligomer or polymer containing two or more photocurable groups per molecule.

By containing the photocurable polyfunctional compound, three-dimensional crosslinking is possible. When the (meth)acrylic acid ester-based polymer is photocurable, an increase in the molecular weight of the (meth)acrylic acid ester-based polymer or three-dimensional crosslinking of the (meth)acrylic acid ester-based polymer can be achieved by the reaction of the (meth)acrylic acid ester-based polymer with the photocurable polyfunctional compound.

By containing the photocurable component, adhesion to a substrate, cohesiveness or the like when the pressure-sensitive adhesive layer is formed, can be easily controlled within a desired range.

As the photocurable polyfunctional compound, preferred applicable examples include the following: a bifunctional-type polyfunctional (meth)acrylate-based monomer such as 1,4-butanediol di(meth)acrylate, 1,6-hexanediol di(meth) acrylate, neopentyl glycol di(meth)acrylate, polyethylene glycol di(meth)acrylate, di(meth)acrylate of neopentyl glycol adipate, hydroxypivalic acid neopentylglycol di(meth) acrylate, dicyclopentanyl di(meth)acrylate, caprolactone-modified dicyclopentenyl di(meth)acrylate, ethylene oxide-modified phosphoric acid di(meth)acrylate, di(meth) acryloxyethyl isocyanurate, allylcyclohexyl di(meth) acrylate, tricyclodecane dimethanol di(meth)acrylate, dimethyloldicyclopentane di(meth)acrylate, ethylene oxide-modified hexahydrophtalic acid di(meth)acrylate, neopentyl glycol-modified trimethylolpropane di(meth)acrylate, adamantane di(meth)acrylate and 9,9-bis[4-(2-acryloyloxyethoxy)phenyl]fluorene; a trifunctional-type polyfunctional (meth)acrylate-based monomer such as isocyanuric acid ethylene oxide-modified triacrylate, trimethylolpropane tri (meth)acrylate, dipentaerythritol tri(meth)acrylate, propionic acid-modified dipentaerythritol tri(meth)acrylate, pentaerythritol tri(meth)acrylate, propylene oxide-modified trimethylolpropane tri(meth)acrylate, and tris(meth)acryloxyethyl isocyanurate; a tetrafunctional-type polyfunctional (meth)acrylate-based monomer such as diglycerin tetra(meth)acrylate and pentaerythritol tetra(meth)acrylate; a pentafunctional-type polyfunctional (meth)acrylate-based monomer such as propionic acid-modified dipentaerythritol penta(meth)acrylate; a hexafunctional-type polyfunctional (meth)acrylate-based monomer such as dipentaerythritol hexa(meth)acrylate and caprolactone-modified dipentaerythritol hexa(meth)acrylate; and an oligomer which contains several (meth)acryloyl groups per molecule and which has a molecular weight of several hundreds to several thousands, such as urethane (meth)acrylate, polyester (meth) acrylate and epoxy (meth) acrylate.

From the viewpoint of a balance between pressure-sensitive adhesion and peel adhesion, an oligomer which contains several (meth)acryloyl groups per molecule and which has a molecular weight of several hundreds to several thousands, such as urethane (meth)acrylate, polyester (meth) acrylate and epoxy (meth)acrylate, is preferably used as the photocurable polyfunctional compound.

The above photocurable polyfunctional compounds can be used alone or in combination of two or more.

In the case of using the photocurable polyfunctional compound, with respect to 100 parts by mass of the pressure-sensitive adhesive such as the (meth)acrylic acid ester-based polymer, the content of the photocurable polyfunctional compound may be 10 parts by mass or more, may be 20 parts by mass or more, or may be 50 parts by mass or more. On the other hand, it may be 300 parts by mass or less, may be 200 parts by mass or less, or may be 150 parts by mass or less.

When the content of the photocurable polyfunctional compound is too small, effects created by the addition may not appear. On the other hand, when the content of the photocurable polyfunctional compound is too large, the properties of the pressure-sensitive adhesive composition, such as storage stability, adhesion to a substrate, pressure-sensitive adhesion and peel properties, may remarkably decrease.

From the viewpoint of a balance of peel adhesion after light irradiation, with respect to the solid content of the pressure-sensitive adhesive composition, the total content of the pressure-sensitive adhesive and the photocurable polyfunctional compound may be 10% by mass or more, or it may be 20% by mass or more, for example. From the viewpoint of pressure-sensitive adhesion and suppressing of contamination of the adherend, with respect to the solid content of the pressure-sensitive adhesive composition, the total content of the pressure-sensitive adhesive and the photocurable polyfunctional compound may be 70% by mass or less, or it may be 60% by mass or less, for example.

(Photoinitiator)

As the photoinitiator, a compound which can generate a radical when it is irradiated with a given amount of light (e.g., UV) can be used. As the compound, examples include, but are not limited to, benzoin, benzoin methyl ether, benzoin ethyl ether, benzoin isopropyl ether, benzoin-n-butyl ether, benzoin isobutyl ether, acetophenone, dimethylaminoacetophenone, 2,2-dimethoxy-2-phenylacetophenone, 2,2-diethoxy-2-phenylacetophenone, 2-hydroxy-2-methyl-1-phenylpropan-1-one, 1-hydroxycyclohexyl phenyl ketone, 2-methyl-1-[4-(methylthio)phenyl]-2-morpholino -propan-1-one, 4-(2-hydroxyethoxy)phenyl-2-(hydroxy-2-propyl) ketone, benzophenone, p-phenylbenzophenone, 4,4'-diethylaminobenzophenone, dichlorobenzophenone, 2-methylanthraquinone, 2-ethylanthraquinone, 2-tertiary -butylanthraquinone, 2-aminoanthraquinone, 2-methylthioxanthone, 2-ethylthioxanthone, 2-chlorothioxanthone, 2,4-dimethylthioxanthone, 2,4-diethylthioxanthone, benzil dimethyl ketal, acetophenone dimethyl ketal, p-dimethylaminobenzoate ester, oligo[2-hydroxy-2-methyl-1[4-(1-methyl vinyl)phenyl]propanone] and 2,4,6-trimethylbenzoyl-diphenyl -phosphine oxide.

From the viewpoint of curing the interior of the coating film and increasing the durability, at least one selected from the group consisting of an acyl phosphine oxide-based initiator, an α-aminoalkylphenone-based initiator, an α-hydroxyketone-based initiator and an oxime ester-based initiator is preferred.

The above photoinitiators may be used alone or in combination of two or more.

From the viewpoint of sufficiently curing the pressure-sensitive adhesive composition, with respect to the solid content of the pressure-sensitive adhesive composition, the content of the photoinitiator may be 0.5% by mass or more, or it may be 1.0% by mass or more, for example. From the viewpoint of a balance between pressure-sensitive adhesion and peel adhesion, with respect to the solid content of the pressure-sensitive adhesive composition, the content of the photoinitiator may be 10.0% by mass or less, or it may be 5.0% by mass or less, for example.

(Thermal Crosslinking Agent)

The pressure-sensitive adhesive composition of the present disclosure preferably further contains a thermal crosslinking agent. The thermal crosslinking agent is a compound which develops a crosslinking reaction by the action of heat.

By containing the thermal crosslinking agent in the pressure-sensitive adhesive composition of the present disclosure, the thermal crosslinking agent is reacted with the crosslinkable group contained in the pressure-sensitive adhesive, thereby eliminating the flowability of the pressure-sensitive adhesive composition after the film formation or controlling the pressure-sensitive adhesion or peel adhesion before light irradiation.

As the thermal crosslinking agent, examples include, but are not limited to, an isocyanate-based crosslinking agent, an epoxy-based crosslinking agent, a melamine-based crosslinking agent, an aziridine-based crosslinking agent, and a metal chelate-based crosslinking agent. From the viewpoint of sufficiently exerting the effects of the present disclosure, an isocyanate-based crosslinking agent and an epoxy-based crosslinking agent are preferred.

As the isocyanate-based crosslinking agent, examples include, but are not limited to, a lower aliphatic polyisocyanate such as butylene diisocyanate and hexamethylene diisocyanate; an alicyclic isocyanate such as cyclopentylene diisocyanate, cyclohexylene diisocyanate and isophorone diisocyanate; an aromatic isocyanate such as 2,4-tolylene diisocyanate, 4,4'-diphenylmethane diisocyanate and xylylene diisocyanate; and an isocyanate adduct such as a trimethylolpropane/tolylene diisocyanate trimer adduct (product name: CORONATE L, manufactured by: Nippon Polyurethane Industry Co., Ltd.), a trimethylolpropane/hexamethylene diisocyanate trimer adduct (product name: CORONATE HL, manufactured by: Nippon Polyurethane Industry Co., Ltd.) and an isocyanurate of hexamethylene diisocyanate (product name: CORONATE HX, manufactured by: Nippon Polyurethane Industry Co., Ltd.)

As the epoxy-based crosslinking agent, examples include, but are not limited to, bisphenol A, epichlorohydrin-type epoxy resin, ethylene glycidyl ether, polyethylene glycol diglycidyl ether, glycerin diglycidyl ether, glycerin triglycidyl ether, 1,6-hexanediol glycidyl ether, trimethylolpropane triglycidyl ether, diglycidyl aniline, diamine glycidyl amine, N,N,N',N'-tetraglycidyl-m-xylenediamine (product name: TETRAD-X, manufactured by: Mitsubishi Gas Chemical Company, Inc.) and 1,3-bis(N,N-diglycidyl aminomethyl)cyclohexane (product name: TETRAD-C, manufactured by: Mitsubishi Gas Chemical Company, Inc.)

The above thermal crosslinking agents may be used alone or in combination of two or more.

From the viewpoint of a balance between pressure-sensitive adhesion and peel adhesion, the content of the thermal crosslinking agent may be appropriately controlled. To obtain the above-mentioned effects, with respect to the solid content of the pressure-sensitive adhesive composition, the content of the thermal crosslinking agent may be 1.0% by mass or more, or it may be 2.0% by mass or more, for example. From the viewpoint of pressure-sensitive adhesion before energy irradiation, with respect to the solid content of the pressure-sensitive adhesive composition, the content of the thermal crosslinking agent may be 10.0% by mass or less, or it may be 8.0% by mass or less, for example.

[Gas Generating Agent of the Present Disclosure]

The pressure-sensitive adhesive composition of the present disclosure contains the gas generating agent of the present disclosure.

Since the gas generating agent of the present disclosure is likely to localize on the surface of a pressure-sensitive adhesive material, the generated gas amount on the surface of the pressure-sensitive adhesive material can be efficiently increased without increasing the content of the gas generating agent in the pressure-sensitive adhesive composition. Accordingly, a decrease in the pressure-sensitive adhesion of the pressure-sensitive adhesive material and clouding of the pressure-sensitive adhesive material are easily suppressed.

From the viewpoint of effectively decreasing the peel adhesion when peeled off, with respect to the solid content of the pressure-sensitive adhesive composition, the content of the gas generating agent of the present disclosure may be 2% by mass or more, or it may be 3% by mass or more, for example. From the viewpoint of suppressing a decrease in the pressure-sensitive adhesion of the pressure-sensitive adhesive material and clouding of the pressure-sensitive adhesive material, with respect to the solid content of the pressure-sensitive adhesive composition, the content of the gas generating agent of the present disclosure may be 40% by mass or less, or it may be 30% by mass or less, for example.

When clouding of the pressure-sensitive adhesive material is suppressed and high transparency is obtained, the pressure-sensitive adhesive composition of the present disclosure obtains a wide range of applications such as accurate checking of appearance and failure with a camera or the like through the pressure-sensitive adhesive layer, and the use of the pressure-sensitive adhesive layer as a removable pressure-sensitive adhesive sheet for processes.

[Solvent]

The pressure-sensitive adhesive composition of the present disclosure may further contain a solvent. By containing the solvent, the property of coating the substrate and the like and the mixing uniformity of the contained components can be improved.

The solvent can be appropriately selected from solvents which are non-reactive with the components in the composition and which are able to dissolve or disperse the components. As the solvent, examples include, but are not limited to, esters, aromatic hydrocarbons, ketones and ethers.

More specifically, from the viewpoint of excellent solubility of (meth)acrylic acid ester-based polymers and easy handling, the solvent may be selected from, for example, methyl acetate, ethyl acetate, n-butyl acetate, i-butyl acetate, benzene, toluene, xylene, acetone, cyclohexane, cyclohexanone, methyl ethyl ketone, tetrahydrofuran and combinations thereof.

The content of the solvent may be appropriately controlled from the viewpoint of the property of coating the substrate and the like and the mixing uniformity of the contained components. For example, with respect to the total amount (100% by mass) of the pressure-sensitive adhesive composition containing the solvent, the content of the solvent may be 5% by mass or more and 40% by mass or less.

[Optional Additives]

As needed, the pressure-sensitive adhesive composition of the present disclosure may further contain several kinds of additives, as long as the effects of the present invention are not impaired.

As the additives, examples include, but are not limited to, a crosslinking promoter, an antioxidant, a stabilizer, a viscosity modifier, a tackifier resin and an organic or inorganic filler.

As the crosslinking promoter, examples include, but are not limited to, a triethylamine-based crosslinking promoter, a cobalt naphthenate-based crosslinking promoter, a tin-based crosslinking promoter, a zinc-based crosslinking promoter, a titanium-based crosslinking promoter and a zirconium-based crosslinking promoter. When the crosslinking agent is an isocyanate-based crosslinking agent, a zinc-based, titanium-based or zirconium-based promoter such as an alkoxide, an acylate and a complex, or a tin-based promoter such as stannous chloride, tetra-n-butyl tin, stannic chloride, trimethyltin hydroxide dimethyltin dichloride and di-n-butyltin dilaurate is preferably used.

As the antioxidant, examples include, but are not limited to, a phenol-based antioxidant.

[Production of Pressure-Sensitive Adhesive Composition]

The method for producing the pressure-sensitive adhesive composition is not particularly limited.

The pressure-sensitive adhesive composition can be obtained by mixing the above-described components and the additives added as needed in a desired order and dissolving or dispersing them. The components can be mixed by use or a mixer or kneader such as a dispersion mixer, a planetary mixer and a butterfly mixer.

[Applications of Pressure-Sensitive Adhesive Composition]

The applications of the pressure-sensitive adhesive composition of the present disclosure are not particularly limited. The pressure-sensitive adhesive composition of the present disclosure can be preferably used in the pressure-sensitive adhesive layer of the pressure-sensitive adhesive sheet described later, and it can be preferably used in the applications of the pressure-sensitive adhesive sheet described later.

In addition, the pressure-sensitive adhesive composition of the present disclosure can be used in a pressure-sensitive adhesive material not in a sheet form, such as an adhesive for temporary adhesion.

C. Pressure-Sensitive Adhesive Sheet

The pressure-sensitive adhesive sheet of one embodiment of the present disclosure is a pressure-sensitive adhesive sheet comprising a pressure-sensitive adhesive layer and a substrate or release sheet on one surface of the pressure-sensitive adhesive layer, wherein the pressure-sensitive adhesive layer is a pressure-sensitive adhesive composition comprising a pressure-sensitive adhesive component and the gas generating agent of the present disclosure, or a cured product of the pressure-sensitive adhesive composition, and wherein the pressure-sensitive adhesive layer has a property that a decrease in pressure-sensitive adhesion from an initial pressure-sensitive adhesion is caused by light irradiation.

Figure 2:
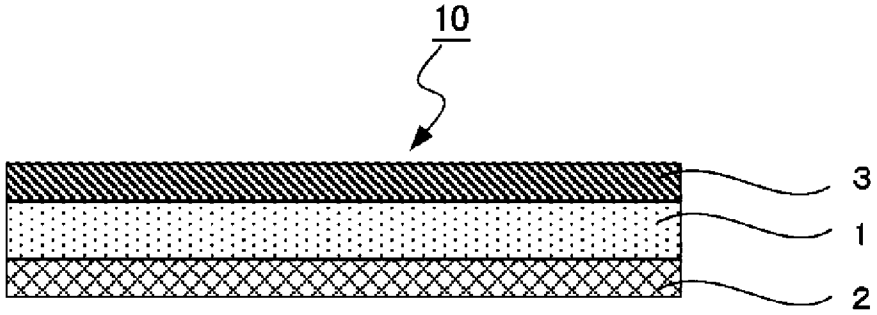
FIG. 2 is a schematic sectional view of another example of the pressure-sensitive adhesive sheet of the present disclosure.

Each of FIGS. 1 and 2 shows a schematic sectional view of an example of the pressure-sensitive adhesive sheet of present disclosure.

A pressure-sensitive adhesive sheet 10 shown in FIG. 1, which is the pressure-sensitive adhesive sheet of the present disclosure, includes a pressure-sensitive adhesive layer 1 and a substrate or release sheet 2 disposed on one surface of the pressure-sensitive adhesive layer 1.

The pressure-sensitive adhesive sheet 10 shown in FIG. 2, which is the pressure-sensitive adhesive sheet of the present disclosure, includes a pressure-sensitive adhesive layer 1, a substrate or release sheet 2 disposed on one surface of the pressure-sensitive adhesive layer 1, and a release sheet 3 disposed on the surface on the opposite side of the pressure-sensitive adhesive layer 1 to the substrate or release sheet 2 side. For easy handling, the release sheet may be attached to the surface on the opposite side of the pressure-sensitive adhesive layer to the substrate or release sheet 2 side, until the pressure-sensitive adhesive sheet of the present disclosure is attached to the adherend.

[Pressure-Sensitive Adhesive Layer]

The pressure-sensitive adhesive layer of the pressure-sensitive adhesive sheet of the present disclosure is a pressure-sensitive adhesive composition containing a pressure-sensitive adhesive component and the gas generating agent of the present disclosure, or a cured product of the pressure-sensitive adhesive composition.

The pressure-sensitive adhesive composition containing the pressure-sensitive adhesive component and the gas generating agent of the present disclosure is not described here since it may be the same as the pressure-sensitive adhesive composition of the present disclosure.

When the pressure-sensitive adhesive composition contains a curable pressure-sensitive adhesive component, the pressure-sensitive adhesive layer of the pressure-sensitive adhesive sheet of the present disclosure may be a cured product of the pressure-sensitive adhesive composition.

The thickness of the pressure-sensitive adhesive layer can be appropriately controlled depending on the intended use. From the removability of the pressure-sensitive adhesive layer, the thickness of the pressure-sensitive adhesive layer is 100 μm or less, for example, and it may be 90 μm or less or may be 80 μm or less. On the other hand, from the viewpoint of exerting pressure-sensitive adhesion, the thickness of the pressure-sensitive adhesive layer is 10 μm or more, for example, and it may be 20 μm or more or may be 40 μm or more.

As the initial pressure-sensitive adhesion of the pressure-sensitive adhesive layer before subjected to light irradiation, the peel adhesion from a glass plate (product name: alkali-free glass OA-11, manufactured by Nippon Electric Glass Co., Ltd.) at a peel rate of 300 ram/min and a peel angle of 180 degrees, may be 0.1 N/25 mm or more, or it may be 0.2 N/25 mm or more. On the other hand, the peel adhesion at a peel angle of 180 degrees may be 30 N/25 mm or less, or it may be 20 N/25 mm or less.

As the pressure-sensitive adhesion of the pressure-sensitive adhesive layer after subjected to light irradiation, the peel adhesion from the glass plate (product name: alkali-free glass OA-11, manufactured by: Nippon Electric Glass Co., Ltd.) at a peel rate of 300 mm/min and a peel angle of 180 degrees may be 0 N/25 mm or more, or it may be 0.01 N/25 mm or more. On the other hand, the peel adhesion at a peel angle of 180 degrees may be 1 N/25 mm or less, or it may be 0.1 N/25 mm or less. The light irradiance may be appropriately selected. For example, the pressure-sensitive adhesion after subjected to UV irradiation at an exposure of 3000 $mJ/cm^2$ may be used as a benchmark of the pressure-sensitive adhesion after subjected to light irradiation.

In general, the peel adhesion increases as the peel rate increases.

The total light transmittance of the pressure-sensitive adhesive layer before subjected to light irradiation is preferably 80% or more, and more preferably 90% or more. The haze of the pressure-sensitive adhesive layer before subjected to light irradiation is preferably 1.5% or less, and more preferably 1.0% or less. In the present disclosure, the total light transmittance can be measured in accordance with JIS K7361-1. For example, it can be measured by a haze meter (such as HM150 manufactured by Murakami Color Research Laboratory Co., Ltd.) Also, the haze value can be measured by a method in accordance with JIS K-7136. For example, it can be measured by a haze meter (such as HM150 manufactured by Murakami Color Research Laboratory Co., Ltd.)

When the haze value is in the above-described range, the transparency of the pressure-sensitive adhesive layer is excellent, and the adherend can be accurately checked or examined by a camera or the like, with the pressure-sensitive adhesive sheet attached thereto.

The presence of the pressure-sensitive adhesive component and the gas generating agent of the present disclosure in the pressure-sensitive adhesive layer can be checked by obtaining a sample from the pressure-sensitive adhesive layer and analyzing the obtained sample. The method for analyzing the sample is preferably LC-MS, for example. Also, preparative liquid chromatography, preparative gel permeation chromatography, NMR, IR, GC-MS, XPS, TOF-SIMS or a combination thereof may be used as the analyzing method.

[Substrate]

The substrate used in the pressure-sensitive adhesive sheet of the present disclosure is not particularly limited, and it may be appropriately selected. A transparent substrate is preferred since the pressure-sensitive adhesion of the pressure-sensitive adhesive layer is preferably decreased from the initial pressure-sensitive adhesion by applying light from the substrate side of the pressure-sensitive adhesive sheet.

The total light transmittance of the substrate used in the pressure-sensitive adhesive sheet of the present disclosure is 80% or more, and more preferably 90% or more. The haze of the substrate used in the pressure-sensitive adhesive sheet of the present disclosure is preferably 1.5% or less, and more preferably 1.0% or less.

The substrate used in the pressure-sensitive adhesive sheet of the present disclosure is preferably a heat-resistant substrate. As the substrate, examples include, but are not limited to, a film made of polyester resin (such as polyethylene terephthalate, polyethylene naphthalate and polybutylene terephthalate), and a film made of polyimide resin, polycarbonate resin, polystyrene resin, polyamide resin, polyetherimide resin, polyether ketone resin, polyphenylene sulfide resin, polyacrylate resin, polyester ether resin, polyamideimide resin, polymethyl methacrylate resin, fluorine resin or the like. From the viewpoint of economic efficiency and performance, the substrate is preferably a film made of polyethylene terephthalate.

The substrate may have a single-layer or multi-layer structure.

To increase the adhesion to the pressure-sensitive adhesive layer, a surface of the substrate, on which the pressure-sensitive adhesive layer will be disposed, may be surface-treated.

The thickness of the substrate is not particularly limited, and it may be appropriately selected depending on the intended use of the pressure-sensitive adhesive sheet. For example, the thickness of the substrate may be such a thickness that allows the substrate to function as a support. For example, the thickness that has been used as the thickness of substrate films, such as a thickness of about 10 μm to 200 μm, is preferably used.

[Release Sheet]

The release sheet is not particularly limited, as long as it can be peeled off from the pressure-sensitive adhesive layer. The release sheet may have a strength that can protect the pressure-sensitive adhesive layer. As such a release sheet, examples include, but are not limited to, a release film and a release paper. A commercially-available product may be used as the release sheet, and the release sheet may have a single-layer or multi-layer structure.

As the single-layer release sheet, examples include, but are not limited to, a release PET film and a fluorine resin-based film.

As the multi-layer release sheet, examples include, but are not limited to, a laminate such that a release layer is disposed on one surface or both surfaces of a substrate layer. As the substrate layer, examples include, but are not limited to, a resin film of polypropylene, polyethylene, polyethylene terephthalate or the like, and a paper such as high-quality paper, coated paper and impregnated paper. The material for the release layer is not particularly limited, as long as it is a material having releasability, such as a silicone compound, an organic compound-modified silicone compound, a fluorine compound, an amino alkyd compound, a melamine compound, an acrylic compound, a polyester compound and a long-chain alkyl compound. These compounds may be emulsion-type, solvent-type or solventless-type compounds.

The thickness of the release sheet may be about 15 μm to 200 μm, for example.

[Method for Producing Pressure-Sensitive Adhesive Sheet]

The pressure-sensitive adhesive sheet of the present disclosure may be produced by any appropriate method.

The pressure-sensitive adhesive sheet of the present disclosure can be obtained by producing a laminate of the pressure-sensitive adhesive layer and the substrate or release sheet. Such a laminate can be produced by any appropriate method such as:

(1) Producing the pressure-sensitive adhesive layer by applying a solution or hot-melt solution of the pressure-sensitive adhesive composition onto the substrate or release sheet;

(2) Producing the pressure-sensitive adhesive layer is formed by applying the solution onto the release sheet in accordance with the method (1) and then transferred onto the substrate;

(3) Producing the pressure-sensitive adhesive layer by extruding the pressure-sensitive adhesive composition onto the substrate; and (4) Producing the substrate layer and the pressure-sensitive adhesive layer in the form of double or multiple layers by extrusion.

Of them, the production method (1) is preferred.

As needed, the surface of the substrate used in the pressure-sensitive adhesive sheet of the present disclosure may be surface-treated. As the surface treatment, examples include, but are not limited to, the following: (1) discharge treatment such as corona discharge treatment and glow discharge treatment, (2) plasma treatment, (3) flame treatment, (4) ozone treatment, (5) ultraviolet treatment, or ionizing radiation treatment such as electron beam treatment and radiation treatment, (6) surface roughening treatment such as sand mat treatment and hairline treatment, (7) chemical treatment and (8) anchor layer formation. As the anchor layer, polyurethane-based resin, polyester-based resin, acryl-based resin, polyester polyurethane resin or the like is used. The thickness of the anchor layer generally ranges from 0.01 μm to 1.5 μm.

The method for applying the pressure-sensitive adhesive composition onto the substrate or release sheet may be appropriately selected from known methods such as a coating method, a printing method, and a transferring method using a mold. As the coating and printing methods, examples include, but are not limited to, a gravure coating method, a reverse coating method, a knife coating method, a dip coating method, a spray coating method, an air knife coating method, a spin coating method, a roller coating method, a printing method, a dipping method, a curtain coating method, a die coating method, a casting method, a bar coating method, an extrusion coating method and an E-type coating method.

As needed, the solvent is appropriately removed (by drying) from the pressure-sensitive adhesive composition layer formed on the substrate or release sheet, followed by heating the pressure-sensitive adhesive composition layer to thermally crosslink the thermal crosslinking agent, thereby producing the pressure-sensitive adhesive layer.

The pressure-sensitive adhesive sheet of the present disclosure includes the pressure-sensitive adhesive layer which is the pressure-sensitive adhesive composition containing the pressure-sensitive adhesive component and the gas generating agent of the present disclosure or which is a cured product of the pressure-sensitive adhesive composition. Accordingly, it is a pressure-sensitive adhesive sheet which can, by the same action as described above, decrease the peel adhesion from the adherend when peeled off, while having sufficient pressure-sensitive adhesion in use, and which shows excellent easy peel properties from the adherend. In addition, since the content of the gas generating agent is small, the pressure-sensitive adhesive layer is less likely to cause clouding and has high transparency.

The pressure-sensitive adhesive sheet of the present disclosure excels in easy peel properties from the adherend after use. Accordingly, it can be used as a suitable pressure-sensitive adhesive sheet in the following cases, for example:

the case where the adherend itself or the surface of a protected member is likely to be damaged along with the following resulting from elaboration or complication of various kinds of electronic and optical members: the reduction of the thickness of the adherend itself, the integration of functions, and miniaturization of the adherend itself, and the case where a surface of the adherend, which is on the side where a protection sheet will be attached, has a wide large area, and large power is needed to peel off the protection sheet from the adherend.

Due to the above-described characteristics, the pressure-sensitive adhesive sheet of the present disclosure can be suitably used in process pressure-sensitive adhesive materials directed to high adhesion and easy peel, such as a removable pressure-sensitive protection sheet for the process of protecting the following: a support for temporary fixation during a thick wafer polishing process in a semiconductor chip production process, a support for temporary fixation when dicing a thin wafer into semiconductor chips, a support for temporary fixation when cutting a sheet, which is obtained by pressure-bonding sheets, into chips in a multi-layer ceramic capacitor (MLCC) production process, a support for temporary fixation in a flexible printed circuit production process, and a process removable pressure-sensitive adhesive protection sheet for protecting the surface of the substrate in a flexible printed circuit production process or a flexible organic EL display production process.

EXAMPLES

Hereinafter, the present disclosure will be described in detail with reference to examples. The embodiments of the present disclosure are not limited to these examples.

The chemical structure of the compounds produced in the following examples was confirmed by $^{1}$H-NMR measurement (device: AVANCE 400 MHz, manufactured by: Bruker Corporation).

Production Example 1: Production of Compound 1 (Gas Generating Agent)

First, 15.61 g of methyl ethyl ketone (MEK, manufactured by Showa Ink Manufacturing Co., Ltd.), 2 g (0.0112 mol) of 5-mercapto-1-phenyl-1H tetrazole (manufactured by Tokyo Chemical Industry Co., Ltd.), 4.69 g (0.0112 mol) of 2-(perfluorohexyl)ethyl acrylate (VISCOAT 13F manufactured by Osaka Organic Chemical Industry Ltd.) and 0.1 g of dimethylphenylphosphine (a catalyst, 6 mol % with respect to acrylate) were put in a reactor equipped with a cooling tube, an addition funnel, a nitrogen inlet, a mechanical stirrer and a digital thermometer. After nitrogen bubbling for 10 minutes, the mixture was stirred at 80° C. for 6 hours under a nitrogen atmosphere.

Then, the temperature of the mixture after 6 hours was returned to room temperature; the mixture was separated with MEK and pure water; the MEK was removed by distillation; and the residue was dried under vacuum, thereby obtaining 5.95 g (0.010 mol, yield 89%) of a compound 1 represented by the following formula. By $^{1}$H-NMR (solvent: $CDCl_3$), it was confirmed that the target product was synthesized.

NMR chemical shift ppm (multiplicity, proton number): 7.50-7.57 (m, 5H), 4.40-4.44 (m, 2H), 3.60-3.64 (m, 2H), 3.0-3.10 (m, 2H), 2.50-2.60 (m, 2H)

Compound 1

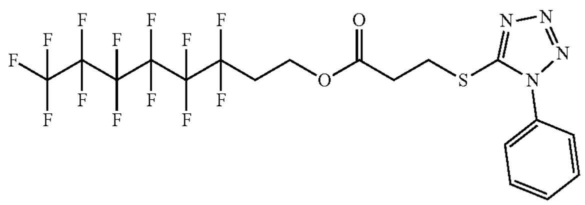

Production Example 2: Production of Compound 2 (Gas Generating Agent)

Also, 5.4 g (0.0108 mol, yield 97%) of a compound 2 represented by the following formula was obtained in the same manner as Production Example 1, except that 3.57 g (0.0112 mol) of 2-(perfluorobutyl)ethyl acrylate (manufactured by Tokyo Chemical Industry Co., Ltd.) was used instead of 2-(perfluorohexyl)ethyl acrylate. By $^{1}$H-NMR (solvent: $CDCl_3$), it was confirmed that the target product was synthesized.

NMR chemical shift ppm (multiplicity, proton number): 7.50-7.57 (m, 5H), 4.40-4.44 (m, 2H), 3.60-3.64 (m, 2H), 3.0-3.10 (m, 2H), 2.50-2.60 (m, 2H)

Compound 2

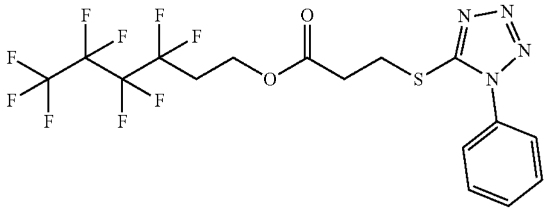

Production Example 3: Production of Compound 3 (Gas Generating Agent)

(1) Synthesis of Intermediate Compound 1 (5-mercapto-1-naphthyl-1H tetrazole) of Compound 3

First, 500 g of acetonitrile (manufactured by FUJIFILM Wako Pure Chemical Corporation), 25 g (0.135 mol) of 1-naphthyl isothiocyanate ((manufactured by Tokyo Chemical Industry Co., Ltd.), 25 g (0.162 mol) of sodium azide (manufactured by FUJIFILM Wako Pure Chemical Corporation) and 22.1 g (0.162 mol) of zinc chloride (manufactured by FUJIFILM Wako Pure Chemical Corporation) were put in a reactor equipped with a cooling tube, an addition funnel, an Ar inlet, a mechanical stirrer and a digital thermometer. After Ar bubbling for 10 minutes, the mixture was stirred at 80° C. for 2 hours under an Ar atmosphere.

Then, the temperature of the mixture after 2 hours was returned room temperature; a reaction solution thus obtained was concentrated at 35° C.; 500 mL of 5 wt. % NaOH aqueous solution was added thereto; the mixed solution was stirred at room temperature for 30 minutes; undesired substances were removed therefrom by suction filtration; the resultant solution was washed three times with chloroform for removal of an organic layer; 40 mL of concentrated hydrochloric acid was added thereto in a dropwise manner; the resultant solution was stirred for 10 minutes at 0° C. to 10° C.; the resultant solution was washed and dried by suction filtration using 150 mL of ion-exchanged water; 500 mL of acetonitrile was added again, and the resultant product was suspended and washed; and the resultant product was concentrated, subjected to suction filtration and then dried under reduced pressure, thereby obtaining 13.6 g (0.060 mol, yield 44.2%) of an intermediate compound 1 represented by the following formula. By $^1$H-NMR (solvent: DMSO-$d_6$), it was confirmed that the target product was synthesized.

NMR chemical shift ppm (multiplicity, proton number): 8.23-8.25 (d, 1H), 8.12-8.15 (d, 1H), 7.59-7.80 (m, 4H), 7.42-7.45 (d, 1H)

(2) Synthesize of Compound 3 (Gas Generating Agent)

Also, 6.50 g (0.0101 mol, yield 90%) of a compound 3 represented by the following formula was obtained in the same manner as Production Example 1, except that 2.55 g (0.0112 mol) of the intermediate compound 1 was used instead of 5-mercapto-1-phenyl-1H tetrazole. By $^1$H-NMR (solvent: $CDCl_3$), it was confirmed that the target product was synthesized.

NMR chemical shift ppm(multiplicity, proton number): 8.07-8.10 (d, 1H), 7.97-8.00 (d, 1H), 7.50-7.60 (m, 5H), 4.40-4.44 (m, 2H), 3.60-3.64 (m, 2H), 3.0-3.10 (m, 2H), 2.50-2.60 (m, 2H)

Compound 3

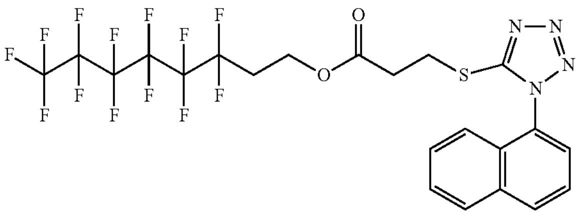

Comparative Production Example 1: Production of Comparative Compound 1

Also, 5.68 g (0.0106 mol, yield 95%) of a comparative compound 1 represented by the following formula was obtained in the same manner as Production Example 1, except that 1.3 g (0.0112 mol) of 5-mercapto-1-methyl-1H tetrazole (manufactured by Tokyo Chemical Industry Co., Ltd.) was used instead of 5-mercapto-1-phenyl-1H tetrazole. By $^1$H-NMR (solvent: $CDCl_3$), it was confirmed that the target product was synthesized.

NMR chemical shift ppm (multiplicity, proton number): 4.40-4.44 (m, 2H), 4.00-4.10 (s, 3H), 3.60-3.64 (m, 2H), 3.0-3.10 (m, 2H), 2.50-2.60 (m, 2H)

Comparative Compound 1

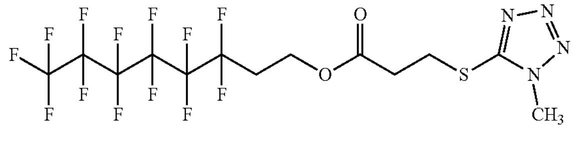

Comparative Production Example 2: Production of Comparative Compound 2

Also, 2.99 g (0.0108 mol, yield 96%) of a comparative compound 2 represented by the following formula was obtained in the same manner as Production Example 1, except that 1.12 g (0.0112 mol) of ethyl acrylate (manufactured by Tokyo Chemical Industry Co., Ltd.) was used instead of 2-(perfluorohexyl)ethyl acrylate. By $^1$H-NMR (solvent: $CDCl_3$), it was confirmed that the target product was synthesized.

NMR chemical shift ppm (multiplicity, proton number): 4.35-4.40 (t, 2H), 3.55-3.60 (t, 2H), 3.0-3.10 (t, 2H), 2.40-2.60 (m, 3H)

Comparative Compound 2

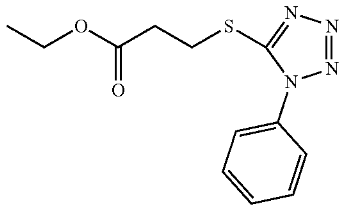

As a comparative compound 3, 5-mercapto-1-phenyl-1H tetrazole (manufactured by Tokyo Chemical Industry Co., Ltd.) was prepared.

Comparative Compound 3

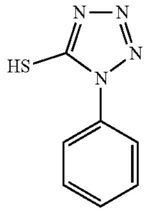

[Evaluation]

<Molar Absorption Coefficient>

The value of the molar absorption coefficient was obtained as follows: 0.1 mM of the obtained compound was dissolved in ethyl acetate; an absorption spectrum in a wavelength range of from 230 nm to 800 nm was measured by use of a ultraviolet-visible spectrophotometer (ultraviolet-visible spectrophotometer UV2700 manufactured by Shimadzu Corporation); using the absorbance in the obtained absorption spectrum, the molar absorption coefficient was calculated by the following formula:

$$\varepsilon = A/c \times d$$

(where ε is molar absorption coefficient; A is absorbance; c is mol concentration; and d is cell thickness).

Table 3 shows the maximum molar absorption coefficient value at a wavelength of 240 nm to 450 nm and the terminal absorption wavelength on the long-wavelength side where the absorbance was 0.01.

<Presence/Absence of Gas Generation>

For each of the above-obtained compounds 1 to 3 and comparative compounds 1 to 3, the presence/absence of gas generation was evaluated as follows: 100 parts by mass of a (meth)acrylic acid ester-based polymer (product name: SK-DYNE 1811L, manufactured by: Soken Chemical & Engineering Co., Ltd.), 6 parts by mass of a thermal crosslinking agent (an isocyanate-based crosslinking agent, product name: CORONATE L, manufactured by: Nippon Polyurethane Industry Co., Ltd.), 39.4 parts by mass of the compound and 486.77 parts by mass of a solvent (product name: KT-11, manufactured by: Showa Ink Manufacturing Co., Ltd.) were mixed. The mixture was applied onto a PET substrate (product name: LUMIRROR U34, 75 μm, manufactured by Toray Industries, Inc.) by an applicator (manufactured by: Yoshimitsu Seiki) so as to obtain a thickness of 50 μm when dried. They were heated in an oven at 80° C. for 3 minutes to obtain a pressure-sensitive adhesive layer. Then, the pressure-sensitive adhesive sheet was cut to a width of 25 mm, and the release PET film was peeled therefrom. The pressure-sensitive adhesive layer side of the pressure-sensitive adhesive sheet was attached to a glass plate adherend (product name: ALKALI-FREE GLASS OA-11, manufactured by: Nippon Electric Glass Co., Ltd.) by pressing them back and forth with a 2 kg roller (manufactured by: Tester Sangyo Co., Ltd.) The resultant product was left to stand for 3 hours in a condition of 23° C. and a humidity of about 60%. Then, it was subjected to UV irradiation at an exposure of 3000 mJ/$cm^2$ using a ultra-high pressure mercury lamp to observe whether or not bubbles were generated at the interface with the glass adherend.

(Evaluation Criteria for the Presence/Absence of Gas Generation)

o: A gas was generated.

x: No gas was generated.

TABLE 3

| | Compound | Maximum molar absorption coefficient ($M^{-1}$ $cm^{-1}$) at 240 nm to 450 nm | Terminal absorption wavelength (nm) (Absorbance = 0.01) | Presence/absence of gas generation |
|---|---|---|---|---|
| Production Example 1 | Compound 1 | 9124 | 335 | ○ |
| Production Example 2 | Compound 2 | 10224 | 338 | ○ |
| Production Example 3 | Compound 3 | 19134 | 424 | ○ |
| Comparative Production Example 1 | Comparative Compound 1 | 5582 | 307 | x |
| Comparative Production Example 2 | Comparative Compound 2 | 22016 | 332 | ○ |
| — | Comparative Compound 3 | 7562 | 333 | ○ |

Example 1

(1) Preparation of Pressure-Sensitive Adhesive Composition

The pressure-sensitive adhesive composition 1 of Example 1 was obtained by mixing the following: 100 parts by mass of a (meth)acrylic acid ester-based polymer (product name: SK-DYNE 1811L, manufactured by: Soken Chemical & Engineering Co., Ltd.), 50 parts by mass of a photocurable polyfunctional compound (product name: urethane acrylate U-10PA, manufactured by: Shin-Nakamura Chemical Co., Ltd.), 1.5 parts by mass of a photoinitiator (product name: OMNIRAD 819, manufactured by: IGM Resins B.V.), 6 parts by mass of a thermal crosslinking agent (an isocyanate-based crosslinking agent, product name: CORONATE L, manufactured by: Nippon Polyurethane Industry Co., Ltd.), 39.4 parts by mass of the compound 1 (gas generating agent) of Production Example 1, and 659.19 parts by mass of a solvent (product name: KT-11, manufactured by: Showa Ink Manufacturing Co., Ltd.)

(2) Production of Pressure-Sensitive Adhesive Sheet

The obtained pressure-sensitive adhesive composition 1 was applied onto a PET substrate (product name: LUMIRROR U34, 75 μm, manufactured by: Toray Industries, Inc.) by an applicator (manufactured by: Yoshimitsu Seiki) so as to obtain a thickness of 50 μm when dried. They were heated in an oven at 80° C. for 3 minutes to obtain a pressure-sensitive adhesive layer. Then, a release PET film (product name: E7006, manufactured by: Toyobo Co., Ltd.) was attached to the pressure-sensitive adhesive layer by a clean roller to produce a pressure-sensitive adhesive sheet 1.

Examples 2 and 3

(1) Preparation of Pressure-Sensitive Adhesive Composition

A pressure-sensitive adhesive composition 2 or 3 was obtained in the same manner as "(1) Preparation of pressure-sensitive adhesive composition" of Example 1, except that the compound 1 of Production Example 1 was changed to the compound 2 or 3 of Production Example 2 or 3, respectively.

(2) Production of Pressure-Sensitive Adhesive Sheet

The pressure-sensitive adhesive sheet 2 or 3 of Example 2 or 3 was obtained in the same manner as "(2) Production of pressure-sensitive adhesive sheet" of Example 1, except that the pressure-sensitive adhesive composition 1 was changed to the pressure-sensitive adhesive composition 2 or 3, respectively.

Example 4

(1) Preparation of Pressure-Sensitive Adhesive Composition

A pressure-sensitive adhesive composition 4 was obtained in the same manner as "(1) Preparation of pressure-sensitive adhesive composition" of Example 1, except that 39.4 parts by mass of the compound 1 (gas generating agent) of Production Example 1 was changed to 6.6 parts by mass of the compound 3 (gas generating agent) of Production Example 3.

(2) Production of Pressure-Sensitive Adhesive Sheet

The pressure-sensitive adhesive sheet 4 of Example 4 was obtained in the same manner as "(2) Production of pressure-sensitive adhesive sheet" of Example 1, except that the pressure-sensitive adhesive composition 1 was changed to the pressure-sensitive adhesive composition 4.

Comparative Example 1

(1) Preparation of Comparative Pressure-Sensitive Adhesive Composition

A comparative pressure-sensitive adhesive composition 1 was obtained in the same manner as "(1) Preparation of pressure-sensitive adhesive composition" of Example 1, except that the compound 1 of Production Example 1 was changed to the comparative compound 1 of Comparative Production Example 1.

(2) Preparation of Comparative Pressure-Sensitive Adhesive Sheet

The comparative pressure-sensitive adhesive sheet 1 of Comparative Example 1 was obtained in the same manner as "(2) Production of pressure-sensitive adhesive sheet" of Example 1, except that the pressure-sensitive adhesive composition 1 was changed to the comparative pressure-sensitive adhesive composition 1.

Comparative Example 2

(1) Preparation of Comparative Pressure-Sensitive Adhesive Composition

A comparative pressure-sensitive adhesive composition 2 was obtained in the same manner as "(1) Preparation of pressure-sensitive adhesive composition" of Example 1, except that the compound 1 of Production Example 1 was changed to the comparative compound 2 of Comparative Production Example 2.

(2) Production of Comparative Pressure-Sensitive Adhesive Sheet

The comparative pressure-sensitive adhesive sheet 2 of Comparative Example 2 was obtained in the same manner as "(2) Production of pressure-sensitive adhesive sheet" of Example 1, except that the pressure-sensitive adhesive composition 1 was changed to the comparative pressure-sensitive adhesive composition 2.

Comparative Example 3

(1) Preparation of Comparative Pressure-Sensitive Adhesive Composition

A comparative pressure-sensitive adhesive composition 3 was obtained in the same manner as "(1) Preparation of pressure-sensitive adhesive composition" of Example 1, except that 39.4 parts by mass of the compound 1 (gas generating agent) of Production Example 1 was changed to 6.6 parts by mass of the comparative compound 2 (gas generating agent) of Comparative Production Example 2.

(2) Production of Comparative Pressure-Sensitive Adhesive Sheet

The comparative pressure-sensitive adhesive sheet 3 of Comparative Example 3 was obtained in the same manner as "(2) Production of pressure-sensitive adhesive sheet" of Example 1, except that the pressure-sensitive adhesive composition 1 was changed to the comparative pressure-sensitive adhesive composition 3.

Comparative Example 4

(1) Preparation of Comparative Pressure-Sensitive Adhesive Composition

A comparative pressure-sensitive adhesive composition 4 was obtained in the same manner as "(1) Preparation of pressure-sensitive adhesive composition" of Example 1, except that the compound 1 of Production Example 1 was changed to the comparative compound 3 (5-mercapto-1-phenyl-1H tetrazole (manufactured by: Tokyo Chemical Industry Co., Ltd.))

(2) Production of Comparative Pressure-Sensitive Adhesive Sheet

The comparative pressure-sensitive adhesive sheet 4 of Comparative Example 4 was obtained in the same manner as "(2) Production of pressure-sensitive adhesive sheet" of Example 1, except that the pressure-sensitive adhesive composition 1 was changed to the comparative pressure-sensitive adhesive composition 4.

Comparative Example 5

(1) Preparation of Comparative Pressure-Sensitive Adhesive Composition

A comparative pressure-sensitive adhesive composition 5 was obtained in the same manner as "(1) Preparation of pressure-sensitive adhesive composition" of Example 1, except that 39.4 parts by mass of the compound 1 (gas generating agent) of Production Example 1 was changed to 6.6 parts by mass of the comparative compound 3 (5-mercapto-1-phenyl-1H tetrazole).

(2) Production of Comparative Pressure-Sensitive Adhesive Sheet

The comparative pressure-sensitive adhesive sheet 5 of Comparative Example 5 was obtained in the same manner as "(2) Production of pressure-sensitive adhesive sheet" of Example 1, except that the pressure-sensitive adhesive composition 1 was changed to the comparative pressure-sensitive adhesive composition 5.

Comparative Example 6

(1) Preparation of Comparative Pressure-Sensitive Adhesive Composition

A comparative pressure-sensitive adhesive composition 6 was obtained in the same manner as "(1) Preparation of pressure-sensitive adhesive composition" of Example 1, except that 39.4 parts by mass of the compound 1 (gas generating agent) of Production Example 1 was not used.

(2) Production of Comparative Pressure-Sensitive Adhesive Sheet

The comparative pressure-sensitive adhesive sheet 6 of Comparative Example 6 was obtained in the same manner as "(2) Production of pressure-sensitive adhesive sheet" of Example 1, except that the pressure-sensitive adhesive composition 1 was changed to the comparative pressure-sensitive adhesive composition 6.

TABLE 4

| Pressure-sensitive adhesive composition | | Example 1 | Example 2 | Example 3 | Example 4 |
|---|---|---|---|---|---|
| Main pressure-sensitive adhesive | SK-DYNE 1811L | 100 | 100 | 100 | 100 |
| Polyfunctional monomer | U-10PA | 50 | 50 | 50 | 50 |
| Photoinitiator | OMNIRAD 819 | 1.5 | 1.5 | 1.5 | 1.5 |
| Thermal crosslinking agent | CORONATE L | 6 | 6 | 6 | 6 |
| Gas generating agent | Compound 1 | 39.4 | — | — | — |
| | Compound 2 | — | 39.4 | — | — |
| | Compound 3 | — | — | 39.4 | 6.6 |
| | Comparative Compound 1 | — | — | — | — |
| | Comparative Compound 2 | — | — | — | — |
| | Comparative Compound 3 | — | — | — | — |
| Content (%) of gas generating agent in solid content | | 20 | 20 | 20 | 4 |

| Pressure-sensitive adhesive composition | | Comparative Example 1 | Comparative Example 2 | Comparative Example 3 | Comparative Example 4 | Comparative Example 5 | Comparative Example 6 |
|---|---|---|---|---|---|---|---|
| Main pressure-sensitive adhesive | SK-DYNE 1811L | 100 | 100 | 100 | 100 | 100 | 100 |
| Polyfunctional monomer | U-10PA | 50 | 50 | 50 | 50 | 50 | 50 |
| Photoinitiator | OMNIRAD 819 | 1.5 | 1.5 | 1.5 | 1.5 | 1.5 | 1.5 |
| Thermal crosslinking agent | CORONATE L | 6 | 6 | 6 | 6 | 6 | 6 |
| Gas generating agent | Compound 1 | — | — | — | — | — | — |
| | Compound 2 | — | — | — | — | — | — |
| | Compound 3 | — | — | — | — | — | — |
| | Comparative Compound 1 | 39.4 | — | — | — | — | — |
| | Comparative Compound 2 | — | 39.4 | 6.6 | — | — | — |
| | Comparative Compound 3 | — | — | — | 39.4 | 6.6 | — |
| Content (%) of gas generating agent in solid content | | 20 | 20 | 4 | 20 | 4 | 0 |

[Evaluation]

<Presence/Absence of Gas Generation>

The pressure-sensitive adhesive sheet was cut to a width of 25 mm, and the release PET film was peeled therefrom. The pressure-sensitive adhesive layer side of the pressure-sensitive adhesive sheet was attached to a glass plate adherend (product name: ALKALI-FREE GLASS OA-11, manufactured by: Nippon Electric Glass Co., Ltd.) by pressing them back and forth with a 2 kg roller (manufactured by: Tester Sangyo Co., Ltd.) The resultant product was left to stand for 3 hours in a condition of 23° C. and a humidity of about 60%. Then, it was subjected to UV irradiation at an exposure of 3000 mJ/cm$^2$ using a ultra-high pressure mercury lamp to observe whether or not bubbles were generated at the interface with the glass adherend.

(Evaluation Criteria for the Presence/Absence of Gas Generation)

o: A gas was generated.

x: No gas was generated.

<Evaluation for Peel Adhesion of Pressure-Sensitive Adhesive Layer>

The pressure-sensitive adhesive sheet was cut to a width of 25 mm, and the release PET film was peeled therefrom. The pressure-sensitive adhesive layer side of the pressure-sensitive adhesive sheet was attached to a glass plate adherend (product name: ALKALI-FREE GLASS OA-11, manufactured by: Nippon Electric Glass Co., Ltd.) by pressing them back and forth with a 2 kg roller (manufactured by: Tester Sangyo Co., Ltd.) The resultant product was left to stand for 3 hours in a condition of 23° C. and a humidity of about 60%; it was measured for the peel adhesion before subjected to UV irradiation (i.e., the initial peel adhesion); it was subjected to UV irradiation at an exposure of 3000 mJ/cm$^2$ using a ultra-high pressure mercury lamp; and then, it was measured for the peel adhesion after subjected to UV irradiation.

The peel adhesion was measured in by a 180° tensile test (travel speed 300 mm/min, peel angle 180 degrees, travel distance 50 mm) using a TENSILON (product name: RTF-1150-H, manufactured by: A&D Co., Ltd.)

<Condition of Pressure-Sensitive Adhesive Layer>

The total light transmittance of the pressure-sensitive adhesive sheet before subjected to UV irradiation was measured by a haze mater (product name: HM150, manufactured by: Murakami Color Research Laboratory Co., Ltd.) in accordance with JIS K7361-1.

(Evaluation Criteria for the Pressure-Sensitive Adhesive Layer Condition)

Transparent: The total light transmittance was 80% or more.

Clouding: The total light transmittance was less than 80%.

TABLE 5

| Example | Gas generating agent | Presence/absence of gas generation | Peel adhesion (gf/25 mm) Before subjected to UV irradiation | Peel adhesion (gf/25 mm) After subjected to UV irradiation (3000 mJ) | Condition of pressure-sensitive adhesive layer |
|---|---|---|---|---|---|
| Example 1 | Compound 1 | o | 44.9 | 1.8 | Transparent |
| Example 2 | Compound 2 | o | 194.8 | 2.6 | Transparent |
| Example 3 | Compound 3 | o | 42.8 | 1.5 | Transparent |
| Example 4 | Compound 3 | o | 502.9 | 2.9 | Transparent |
| Comparative Example 1 | Comparative Compound 1 | x | 42.3 | 11.2 | Transparent |
| Comparative Example 2 | Comparative Compound 2 | o | 459.0 | 5.2 | Transparent |
| Comparative Example 3 | Comparative Compound 2 | x | 653.8 | 6.0 | Transparent |
| Comparative Example 4 | Comparative Compound 3 | o | 1045.5 | 87.0 | Clouding |
| Comparative Example 5 | Comparative Compound 3 | x | 485.5 | 10.0 | Transparent |
| Comparative Example 6 | None | x | 690.5 | 5.6 | Transparent |

(Results)

For the pressure-sensitive adhesive sheets of Examples 1 to 4, each of which included the pressure-sensitive adhesive layer that was a cured product of the pressure-sensitive adhesive composition mixed with the gas generating agent of the present disclosure, the peel adhesion after subjected to light (UV) irradiation greatly decreased compared to Comparative Examples 1 to 6. In addition, the pressure-sensitive adhesive sheets of Examples 1 to 4 showed excellent easy peel properties, showed no clouding, and showed excellent transparency.

As shown in Example 4, it was revealed that even when the content of the gas generating agent of the present disclosure in the solid content of the pressure-sensitive adhesive layer is as small as 4% by mass, the gas generating agent can efficiently generate gas, and the peel adhesion after subjected to light irradiation greatly decreases while the pressure-sensitive adhesion before subjected to light irradiation is kept high.

For the pressure-sensitive adhesive sheet of Comparative Example 1 in which the comparative compound 1 was used as the gas generating agent, while the gas generating agent localized on the surface of the pressure-sensitive adhesive sheet, gas generation by light irradiation did not appear, and a decrease in the peel adhesion after subjected to light irradiation was insufficient. For the pressure-sensitive adhesive sheets of Comparative Examples 2 and 3 in which the comparative compound 2 was used as the gas generating agent, gas generation appeared on the surface of the pressure-sensitive adhesive layer when the content of the gas generating agent in the solid content of the pressure-sensitive adhesive layer was 20% by mass. However, gas generation did not appear when the content of the gas generating agent in the solid content of the pressure-sensitive adhesive layer was as small as 4% by mass. For the pressure-sensitive adhesive sheets of Comparative Examples 2 and 3, the peel adhesion after subjected to light irradiation was almost the same as that of Comparative Example 6 in which any gas generating agent was not used.

For the pressure-sensitive adhesive sheet of Comparative Example 4 in which the comparative compound 3, which is used in the conventional art, was used as the gas generating agent, gas generation appeared on the surface of the pressure-sensitive adhesive layer; however, the pressure-sensitive adhesive layer showed clouding, and a decrease in the peel adhesion after subjected to light irradiation was insufficient. The reason is thought as follows: since the compatibility of the comparative compound 3 (the gas generating agent) was poor and caused the clouding of the pressure-sensitive adhesive layer, UV curing inhibition was caused. For the pressure-sensitive adhesive sheet of Comparative Example 5 in which the content of the comparative compound 3 (the gas generating agent) in the solid content of the pressure-sensitive adhesive layer was decreased to 4% by mass, gas generation did not appear, and the peel adhesion after subjected to light irradiation was inferior to the pressure-sensitive adhesive sheet of Comparative Example 6 in which any gas generating agent was not used.

REFERENCE SIGNS LIST

1. Pressure-sensitive adhesive layer
2. Substrate or release sheet
3. Release sheet
10. Pressure-sensitive adhesive sheet

The invention claimed is:

1. A gas generating agent which generates a gas by light irradiation, which has a maximum molar absorption coefficient value of 7000 or more at a wavelength of 240 nm to 450 nm, and which is represented by at least one of the following general formulae (1) and (2):

$$A\text{-}L\text{-}Q^1 \quad (1)$$

$$A\text{-}L\text{-}Q^2\text{-}L\text{-}A \quad (2)$$

in the general formulae (1) and (2), each A is independently a gas generating moiety represented by the following general formula (A-1), (A-2) or (A-3); each L is independently a direct bond or a divalent linking group; $Q^1$ is a monovalent fluorinated aliphatic hydrocarbon group in which a number of carbon atoms to which a fluorine atom is directly bound is from 2 to 8, which optionally contains an ether bond (—O—) in a carbon chain, and which optionally contains a substituent, or $Q^1$ is a monovalent organopolysiloxane group; and $Q^2$ is a divalent fluorinated aliphatic hydrocarbon group in which a number of carbon atoms to which a fluorine atom is directly bound is from 2 to 8 and which optionally contains an ether bond (—O—) in a carbon chain, or $Q^2$ is a divalent organopolysiloxane group:

(A-1)

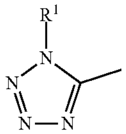

-continued (A-2)

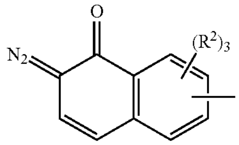

(A-3)

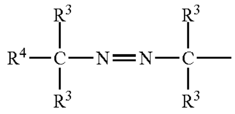

in the general formulae (A-1), (A-2) and (A-3), R 1 is an aromatic group which contains 3 to 20 carbon atoms and which optionally contains a substituent; each $R^2$ is independently a hydrogen atom or a hydrocarbon group which contains 1 to 20 carbon atoms and which optionally contains a substituent; each $R^3$ is independently a hydrocarbon group which contains 1 to 20 carbon atoms and which optionally contains a substituent, a cyano group, —$COOR^5$ or —$CONR^6R^7$; $R^4$ is a hydrocarbon group which contains 1 to 20 carbon atoms and which optionally contains a substituent, a cyano group, —$COOR^5$, —$CONR^6R^7$ or the above-described -L-$Q^1$; each $R^5$ is independently a hydrocarbon group which contains 1 to 20 carbon atoms and which optionally contains a substituent; each $R^7$ is independently a hydrocarbon group which contains 1 to 20 carbon atoms and which optionally contains a substituent; and $R^6$ is a hydrogen atom or a hydrocarbon group which contains 1 to 5 carbon atoms.

2. The gas generating agent according to claim 1, wherein, in the general formulae (1) and (2), $Q^1$ is any one of monovalent fluorinated aliphatic hydrocarbon groups represented by the following formulae (Rf-1) to (Rf-5) or a monovalent organopolysiloxane group represented by the following formula (Si-1), and $Q^2$ is a divalent fluorinated aliphatic hydrocarbon group represented by the following formula (Rf-6) or a divalent organopolysiloxane group represented by the following formula (Si-2):

$$—C_nF_{2n+1} \quad (Rf\text{-}1)$$

$$—C_nF_{2n}H \quad (Rf\text{-}2)$$

$$—C_nF_{2n-1} \quad (Rf\text{-}3)$$

$$—C_{n'}F_{2n'-3} \quad (Rf\text{-}4)$$

$$—C_nF_{2n}—(OC_{n''}F_{2n''})_m—J^1 \quad (Rf\text{-}5)$$

$$—C_nF_{2n}—(OC_{n''}F_{2n''})_m— \quad (Rf\text{-}6)$$

in the formulae (Rf-1), (Rf-2) and (Rf-3), each n is independently an integer of 2 to 8;
in the formula (Rf-4), n' is an integer of 4 to 10;
in the formula (Rf-5), n is an integer of 1 to 8; n" is an integer of 0 to 7; m is an integer of 0 to 7; n+n"×m is an integer of 2 to 8; and $J^1$ is a hydrogen atom, a fluorine atom, a hydroxyl group, an amino group, a carboxy group or a (meth)acryloyloxy group;

in the formula (Rf-6), n is an integer of 0 to 8; n" is an integer of 0 to 4; m is an integer of 0 to 8; and n+n"×m is an integer of 2 to 8;

(Si-1)

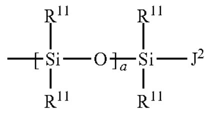

(Si-2)

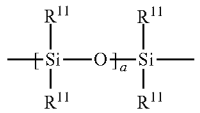

in the formulae (Si-1) and (Si-2), each $R^{11}$ is independently a monovalent hydrocarbon group which contains 1 to 20 carbon atoms and which optionally contains a substituent, a hydrogen atom, a hydroxyl group, an alkoxy group which contains 1 to 20 carbon atoms, or a group represented by the following formula (Si-3); $J^2$ is a monovalent hydrocarbon group which contains 1 to 20 carbon atoms and which optionally contains a substituent, a hydrogen atom, a hydroxyl group, an alkoxy group which contains 1 to 20 carbon atoms, an amino group, a carboxy group or a (meth) acryloyloxy group; and each a is independently a number of 1 to 100; and (Si-3)

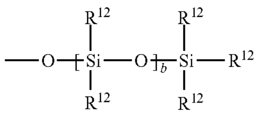

in the formula (Si-3), each $R^{12}$ is independently a monovalent hydrocarbon group which contains 1 to 20 carbon atoms and which optionally contains a substituent, a hydrogen atom, a hydroxyl group or an alkoxy group which contains 1 to 20 carbon atoms, and b is a number of 0 to 100.

3. The gas generating agent according to claim 1, wherein, in the general formulae (1) and (2), each L is independently a direct bond, $—SCH_2CH_2COO—$, $—SCH_2CH(CH_3)COO—$, $—SCH_2CH(OH)CH_2—$, $—OCH_2CH(OH)CH_2—$, $—SCH(CH_3)O—$, $—OCH(CH_3)O—$, —COO—, —CONH—, —COS—, $—SO_2NH—$, or a hydrocarbon group which contains 1 to 22 carbon atoms, which optionally contains at least one selected from the group consisting of —O— and —S—, and which is optionally substituted by a hydroxyl group, or a combination thereof.

4. A pressure-sensitive adhesive composition comprising a pressure-sensitive adhesive component and the gas generating agent defined by claim 1.

5. The pressure-sensitive adhesive composition according to claim 4, further comprising a photocurable component and a photoinitiator.

6. The pressure-sensitive adhesive composition according claim 4, further comprising a thermal crosslinking agent.

7. A pressure-sensitive adhesive sheet comprising a pressure-sensitive adhesive layer and a substrate or release sheet on one surface of the pressure-sensitive adhesive layer, wherein the pressure-sensitive adhesive layer is a pressure-sensitive adhesive composition comprising a pressure-sensitive adhesive component and the gas generating agent defined by claim 1, or a cured product of the pressure-sensitive adhesive composition, and wherein the pressure-sensitive adhesive layer has a property that a decrease in pressure-sensitive adhesion from an initial pressure-sensitive adhesion is caused by light irradiation.

8. The pressure-sensitive adhesive sheet according to claim 7, further comprising a release sheet on a surface on an opposite side of the pressure-sensitive adhesive layer to the substrate or release sheet side.

9. The pressure-sensitive adhesive sheet according to claim 7, wherein the pressure-sensitive adhesive composition further comprises a photocurable component and a photoinitiator.

10. The pressure-sensitive adhesive sheet according to claim 7, wherein the pressure-sensitive adhesive composition further comprises a thermal crosslinking agent.

* * * * *